(12) United States Patent
Daramola et al.

(10) Patent No.: US 8,822,214 B2
(45) Date of Patent: Sep. 2, 2014

(54) CELLS FOR TRANSIENT EXPRESSION AND USES THEREOF

(75) Inventors: Olalekan Daramola, Cambridge (GB); Gregory Dean, Cambridge (GB); Diane Hatton, Cambridge (GB); Jessica Stevenson, Cambridge (GB)

(73) Assignee: MedImmune Limited, Cambridge (GB)

( * ) Notice: Subject to any disclaimer, the term of this patent is extended or adjusted under 35 U.S.C. 154(b) by 30 days.

(21) Appl. No.: 13/395,339

(22) PCT Filed: Sep. 15, 2010

(86) PCT No.: PCT/EP2010/063583
§ 371 (c)(1),
(2), (4) Date: May 17, 2012

(87) PCT Pub. No.: WO2011/033005
PCT Pub. Date: Mar. 24, 2011

(65) Prior Publication Data
US 2012/0231500 A1  Sep. 13, 2012

Related U.S. Application Data

(60) Provisional application No. 61/242,478, filed on Sep. 15, 2009.

(51) Int. Cl.
*C12N 5/00* (2006.01)

(52) U.S. Cl.
USPC .......................................................... 435/325

(58) Field of Classification Search
None
See application file for complete search history.

(56) References Cited

FOREIGN PATENT DOCUMENTS

| EP | 1 851 319 B1 | 3/2009 | |
|---|---|---|---|
| WO | WO 87/04462 | 7/1987 | |
| WO | WO 02/27005 A2 | 4/2002 | |
| WO | WO 03/054172 A2 | 7/2003 | |
| WO | WO 2006/060769 A2 | 6/2006 | |
| WO | WO 2007/048601 | * 5/2007 | ........... C12N 15/869 |
| WO | WO 2007/048601 A1 | 5/2007 | |
| WO | WO 2009/137911 A1 | 11/2009 | |

OTHER PUBLICATIONS

Baldi, L., Muller, N., Picasso, S., Jacquet, R., Girard, P., Thanh, H. P., Derow, E. and Wurm, F. M., *Transient gene expression in suspension HEK-293 cells: Application to large-scale protein production*. Biotechnology Progress, 2005. 21: p. 148-153.
Baldi, L., Hacker, D. L., Adam, M. and Wurm, F.M., *Recombinant protein production by large-scale transient gene expression in mammalian cells: state of the art and future perspectives*. Biotechnology Letters, 2007. 29: p. 677-684.
Birch, J.R., Mainwaring, D.O. and Racher, A.J., *Use of the glutamine synthetase (GS) expression system for the rapid development of highly productive mammalian cell processes*. Chapter 4, pp. 809-832, Modern Biopharmaceuticals (Ed. Knäblein) (c) 2005 Wiley-VCH Verlag GmbH & co. KGaA, Weinheim, 2005.
Butler, M. and Christie, A., Adaptation of mammalian cells to non-ammoniagenic media. Cytotechnology. 1994. 15:87-94.
Cachianes, G., Ho, C., Weber, R.F., Williams, S.R., Goeddel, D.V. and Leung, D.W., *Epstein-Barr virus-derived vectors for transient and stable expression of recombinant proteins*. Biotechniques, 1993. 15(2): p. 255-259.
Chittenden, T., Lupton, S. and Levine, A., J., *Functional limits of OriP, the Epstein-Barr virus plasmid origin of replication*. Journal of Virology, 1989. 63: p. 3016-3025.
Codamo J, Munro TP, Hughes BS, Song M, Gray PP. *Enhanced CHO cell-based transient gene expression with the epi-CHO expression system*. Mol Biotechnol. 2011, 48:109-115.
Derouazi, M., Girard, P., Van Tilbourgh, F., Iglesias, K., Muller, N., Bertschinger, M and Wurm, F.M., *Serum-free large-scale transient transfection of CHO cells*. Biotechnology and Bioengineering, 2004. 87(4): p. 537-545.
Durocher, Y., Perret, S. and Kamen, A., *High-level and high-throughput recombinant protein production by transient transfection of suspension-growing human 293-EBNA1 cells*. Nucleic Acids Research, 2002. 30(2): p. E9.
Enosawa S, Suzuki S, Fujino M, Amemiya H, Omasa T, Urayama S, Tanimura N, Suga K. An attempt to add biological functions by genetic engineering in order to produce high-performance bioreactor cells for hybrid artificial liver: Transfection of glutamine synthetase into Chinese hamster ovary (CHO) cell. Cell Transplant. 1997, 6:537-540.
Frappier L. *Contributions of Epstein-Barr nuclear antigen 1 (EBNA1) to cell immortalization and survival*. Viruses. 2012, 4:1537-1547.
Huang YF, Wang Y, Watford M. Glutamine directly downregulates glutamine synthetase protein levels in mouse C2C12 skeletal muscle myotubes. *J Nutr*. 2007;137:1357-1362.
Jones RJ, Smith LJ, Dawson CW, Haigh T, Blake NW, Young LS. Epstein-Barr virus nuclear antigen 1 (EBNA1) induced cytotoxicity in epithelial cells is associated with EBNA1 degradation and processing. *Virology*. 2003;313:663-676.
Kirchmaier, A.L., and Sugden, B., *Plasmid maintenance of derivatives of OriP of Epstein-Barr virus*. Journal of Virology, 1995. 69(2): p. 1280-1283.
Kishida T, Asada H, Kubo K, Sato YT, Shin-Ya M, Imanishi J, Yoshikawa K, Mazda O. *Pleiotrophic functions of Epstein-Barr virus nuclear antigen-1 (EBNA-1) and oriP differentially contribute to the efficiency of transfection/expression of exogenous gene in mammalian cells*. J Biotechnol. 2008, 133:201-207.

(Continued)

*Primary Examiner* — Catherine Hibbert

(57) ABSTRACT

This invention relates to the transient expression of heterologous polypeptides in mammalian cell lines. Specifically it relates to an expression-enhanced cell line derived from a parent cell line, the expression-enhanced cell line comprising nucleic acid encoding Epstein-Barr Virus Nuclear Antigen 1 or a functional derivative, analogue, or variant thereof; and further comprising:
  (a) a nucleic acid encoding an exogenous glutamine synthetase;
  (b) a nucleic acid encoding an endogenous glutamine synthetase, wherein the endogenous glutamine is arranged to have enhanced enzymatic activity and/or enhanced expression relative to the parent cell line under comparable conditions; or
  (c) both (a) and (b).

19 Claims, 14 Drawing Sheets

(56) References Cited

OTHER PUBLICATIONS

Krysan, P.K., and Calos, M. P., *Epstein-Barr virus-based vectors that replicate in rodent cells.* Gene, 1993. 136: p. 137-143.

Kunaparaju, R., Liao, M and Sunstrom, N.-A., *Epi-CHO, an episomal expression system for recombinant protein production in CHO cells.* Biotechnology and Bioengineering, 2005. 91(6): p. 670-677.

Längle-Rouault, F., Patzel, V., Benavente, A., Taillez, M., Silvestre, N., Bompard, A., Sczakiel, G., Jacobs, E. and Rittner, K., *Up to 100-fold increase of apparent gene expression in the presence of Epstein-Barr virus OriP sequences and EBNA-1: implications of the nuclear import of plasmids.* Journal of Virology, 1998. 72(7): p. 6181-6185.

Liu, C., Dalby, B., Chen, W., Kilzer, J.M. and Chiou, H.C., *Transient transfection for high-level recombinant protein production in suspension cultured mammalian cells.* Molecular Biotechnology, 2008. 39: p. 141-153.

Mates JM, Perez-Gomez C, Nunez de Castro I, Asenjo M, Marquez J. Glutamine and its relationship with intracellular redox status, oxidative stress and cell proliferation/death. *Int J Biochem Cell Biol.* 2002;34:439-458.

Meissner, P., Pick, H., Kulangra, A., Chatellard, P., Freidrich, K. and Wurm, F.M., *Transient gene expression: recombinant protein production with suspension-adapted HEK293-EBNA cells.* Biotechnology and Bioengineering, 2000. 75(2): p. 197-203.

Mizuguchi, H., Hosono, H. and Hayakawa, T., *Long-term replication of Epstein-Barr virus-derived episomal vectors in the rodent cells.* FEBS Letters, 2000. 472: p. 173-178.

Muller, N., Derouazi. M., Van Tilborgh, F., Wulhfard, S., Hacker, D.L., Jordan, M and Wurm, F.M., *Scalable transient gene expression in Chinese hamster ovary cells in instrumented and non-instrumented cultivation systems.* Biotechnology Letters, 2007. 29: p. 703-711.

Prett, J., Daramola, L., Cohen, M., Davies, S., Field, R. and Hatton, D., *Rapid production of IgG from ScFv (Poster).* Second European BioTechnology Workshop, Switzerland., 2002.

Rajendra Y, Kiseljak D, Baldi L, Hacker DL, Wurm FM. Reduced glutamine concentration improves protein production in growth-arrested CHO-DG44 and HEK-293E cells. *Biotechnol Lett.* 2012;34:619-626.

Saeki, Y., Wataya-Kaneda, M., Tanaka, K. and Kaneda, Y., *Sustained transgene expression in vitro and in vivo using an Epstein-Barr virus replicon vector system combined with HVJ liposomes.* Gene Therapy, 1998. 5: p. 1031-1037.

Tomiyasu, K., Satoh, E., Oda, Y., Nishizaki, K., Kondo, M., Imanishi, J. and Mazda, O., *Gene transfer in vitro and in vivo with Epstein-Barr virus-based episomal vector results in markedly high transient expression in rodent cells.* Biochemical and Biophysical Research Communications, 1998. 253: p. 733-738.

Vidal M, Wrighton C, Eccles S, Burke J, Grosveld F. Differences in human cell lines to support stable replication of epstein-barr virus-based vectors. *Biochim Biophys Acta.* 1990;1048:171-177.

Voedisch B, Patoux A, Sterkenburgh J, Buchs M, Barry E, Allard C, Geisse S. About making a CHO production cell line "research-friendly" by genetic engineering. *BMC Proceedings.* 2011; 5 (Suppl 8):p. 132.

Yates, J.L., Warren, N., Reisman, D. and Sugden, B, *A cis-acting element from the Epstein-Barr viral genome that permits stable replication of recombinant plasmids in latently infected cells.* Proc. Natl. Acad. Sci. USA, 1984. 81: p. 3806-3810.

Yates, J.L., Warren, N. and Sugden, B., *Plasmids derived from Epstein-Barr virus replicate stably in a variety of mammalian cells.* Nature (London), 1985. 313: p. 812-815.

\* cited by examiner

SEQUENCE LISTING

```
<160> NUMBER OF SEQ ID NOS: 16

<210> SEQ ID NO 1
<211> LENGTH: 641
<212> TYPE: PRT
<213> ORGANISM: Human herpesvirus 4
<220> FEATURE:
<223> OTHER INFORMATION: EBNA-1

<400> SEQUENCE: 1

Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Gly Ser Gly Pro Gln
            20                  25                  30

Arg Arg Gly Gly Asp Asn His Gly Arg Gly Arg Gly Arg Gly Arg Gly
        35                  40                  45

Arg Gly Gly Gly Arg Pro Gly Ala Pro Gly Gly Ser Gly Ser Gly Pro
    50                  55                  60

Arg His Arg Asp Gly Val Arg Arg Pro Gln Lys Arg Pro Ser Cys Ile
65                  70                  75                  80
```

```
Gly Cys Lys Gly Thr His Gly Thr Gly Ala Gly Ala Gly Ala Gly
                85              90              95

Gly Ala Gly Ala Gly Ala Gly Ala Gly Gly Ala Gly Ala Gly Gly
            100             105             110

Gly Gly Ala Gly Gly Ala Gly Gly Ala Gly Gly Ala Gly Ala Gly
            115             120             125

Gly Ala Gly Ala Gly Gly Ala Gly Gly Ala Gly Gly Ala Gly Ala
        130             135             140

Gly Gly Gly Ala Gly Ala Gly Gly Ala Gly Gly Ala Gly Ala Gly
145             150             155             160

Gly Gly Ala Gly Gly Ala Gly Gly Ala Gly Gly Gly Ala Gly Gly
            165             170             175

Ala Gly Gly Gly Ala Gly Gly Ala Gly Gly Gly Ala Gly Gly Gly
            180             185             190

Ala Gly Gly Ala Gly Ala Gly Gly Ala Gly Ala Gly Gly Ala Gly
            195             200             205

Gly Ala Gly Ala Gly Ala Gly Gly Ala Gly Ala Gly Gly Gly Ala
        210             215             220

Gly Gly Ala Gly Gly Ala Gly Ala Gly Gly Ala Gly Ala Gly Ala
225             230             235             240

Gly Ala Gly Gly Ala Gly Ala Gly Gly Ala Gly Gly Ala Gly Gly
            245             250             255

Gly Ala Gly Gly Ala Gly Ala Gly Gly Ala Gly Gly Ala Gly Gly
            260             265             270

Gly Gly Ala Gly Gly Ala Gly Ala Gly Gly Gly Ala Gly Ala Gly
        275             280             285

Ala Gly Gly Ala Gly Gly Ala Gly Ala Gly Gly Ala Gly Gly Ala
        290             295             300

Ala Gly Gly Ala Gly Gly Ala Gly Ala Gly Gly Ala Gly Ala Gly
305             310             315             320

Gly Ala Gly Ala Gly Gly Gly Gly Arg Gly Arg Gly Ser Gly Gly
            325             330             335

Arg Gly Arg Gly Gly Ser Gly Gly Arg Gly Arg Gly Gly Ser Gly Gly
            340             345             350

Arg Arg Gly Arg Gly Arg Glu Arg Ala Arg Gly Gly Ser Arg Glu Arg
        355             360             365

Ala Arg Gly Arg Gly Arg Gly Arg Gly Glu Lys Arg Pro Arg Ser Pro
        370             375             380

Ser Ser Gln Ser Ser Ser Ser Gly Ser Pro Pro Arg Arg Pro Pro Pro
385             390             395             400

Gly Arg Arg Pro Phe Phe His Pro Val Gly Glu Ala Asp Tyr Phe Glu
            405             410             415

Tyr His Gln Glu Gly Gly Pro Asp Gly Glu Pro Asp Val Pro Pro Gly
            420             425             430

Ala Ile Glu Gln Gly Pro Ala Asp Asp Pro Gly Glu Gly Pro Ser Thr
            435             440             445

Gly Pro Arg Gly Gln Asp Gly Gly Arg Arg Lys Lys Gly Gly Trp
450             455             460

Phe Gly Lys His Arg Gly Gln Gly Gly Ser Asn Pro Lys Phe Glu Asn
465             470             475             480

Ile Ala Glu Gly Leu Arg Ala Leu Leu Ala Arg Ser His Val Glu Arg
            485             490             495
```

Thr Thr Asp Glu Gly Thr Trp Val Ala Gly Val Phe Val Tyr Gly
            500                 505                 510
Ser Lys Thr Ser Leu Tyr Asn Leu Arg Arg Gly Thr Ala Leu Ala Ile
        515                 520                 525
Pro Gln Cys Arg Leu Thr Pro Leu Ser Arg Leu Pro Phe Gly Met Ala
    530                 535                 540
Pro Gly Pro Gly Pro Gln Pro Gly Pro Leu Arg Glu Ser Ile Val Cys
545                 550                 555                 560
Tyr Phe Met Val Phe Leu Gln Thr His Ile Phe Ala Glu Val Leu Lys
                565                 570                 575
Asp Ala Ile Lys Asp Leu Val Met Thr Lys Pro Ala Pro Thr Cys Asn
            580                 585                 590
Ile Arg Val Thr Val Cys Ser Phe Asp Asp Gly Val Asp Leu Pro Pro
        595                 600                 605
Trp Phe Pro Pro Met Val Glu Gly Ala Ala Ala Glu Gly Asp Asp Gly
    610                 615                 620
Asp Asp Gly Asp Glu Gly Gly Asp Gly Asp Glu Gly Glu Glu Gly Gln
625                 630                 635                 640
Glu

<210> SEQ ID NO 2
<211> LENGTH: 1122
<212> TYPE: DNA
<213> ORGANISM: Cricetulus griseus
<220> FEATURE:
<223> OTHER INFORMATION: Glutamine synthetase

<400> SEQUENCE: 2
atggccacct cagcaagttc ccacttgaac aaaaacatca agcaaatgta cttgtgcctg      60
ccccagggtg agaaagtcca agccatgtat atctgggttg atggtactgg agaaggactg     120
cgctgcaaaa cccgcaccct ggactgtgag cccaagtgtg tagaagagtt acctgagtgg     180
aattttgatg gctctagtac ttttcagtct gagggctcca acagtgacat gtatctcagc     240
cctgttgcca tgtttcggga ccccttccgc agagatccca acaagctggt gttctgtgaa     300
gttttcaagt acaaccggaa gcctgcagag accaatttaa ggcactcgtg taaacggata     360
atggacatgg tgagcaacca gcaccccctg tttggaatgg aacaggagta tactctgatg     420
ggaacagatg ggcacccttt tggttggcct tccaatggct ttcctgggcc caaggtccg      480
tattactgtg gtgtgggcgc agacaaagcc tatggcaggg atatcgtgga ggctcactac     540
cgcgcctgct gtatgctggg gtcaagatt acaggaacaa tgctgaggt catgcctgcc       600
cagtgggaat ccaaataggg accctgtgaa ggaatccgca tgggagatca tctctgggtg     660
gcccgtttca tcttgcatcg agtatgtgaa gactttgggg taatagcaac ctttgacccc     720
aagcccattc ctgggaactg gaatggtgca ggctgccata ccaactttag caccaaggcc     780
atgcgggagg agaatggtct gaagcacatc gaggaggcca tcgagaaact aagcaagcgg     840
caccggtacc acattcgagc ctacgatccc aagggggggcc tggacaatgc ccgtcgtctg     900
actgggttcc acgaaacgtc caacatcaac gactttttctg ctggtgtcgc caatcgcagt     960
gccagcatcc gcattccccg gactgtcggc aggagaagaa aggttactt tgaagaccgc      1020
cgccccctctg ccaattgtga ccccttttgca gtgacagaag ccatcgtccg cacatgcctt     1080
ctcaatgaga ctggcgacga gcccttccaa tacaaaaact aa                       1122

<210> SEQ ID NO 3

<211> LENGTH: 354
<212> TYPE: DNA
<213> ORGANISM: Homo sapiens
<220> FEATURE:
<223> OTHER INFORMATION: Antibody A VH

<400> SEQUENCE: 3

```
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtgt attactgtgc aagagatcta   300
attcacgggg tgacgcggaa ctggggccag gggacactgg tcaccgtctc ctca          354
```

<210> SEQ ID NO 4
<211> LENGTH: 346
<212> TYPE: DNA
<213> ORGANISM: Homo sapiens
<220> FEATURE:
<223> OTHER INFORMATION: Antibody A VL

<400> SEQUENCE: 4

```
aattttatgc tgactcagcc ccactctgtg tcggagtctc cggggaagac ggtaaccatc    60
tcctgcaccc gcagcagtgg cagccttgcc aactactatg cgcagtggta ccaacagcgc   120
ccgggcagtt cccccaccat tgtgatcttt gcgaataacc aaagaccctc tggggtccct   180
gatcgattct ctggctccat cgacagctcc tccaactctg cctccctcac catctctgga   240
ctgaagactg aggacgaggc tgactactac tgccagacgt acgaccccta cagcgtggtg   300
ttcggcggag ggaccaagct ggaccaagct gaccgtccta ggtgag                   346
```

<210> SEQ ID NO 5
<211> LENGTH: 363
<212> TYPE: DNA
<213> ORGANISM: Homo sapiens
<220> FEATURE:
<223> OTHER INFORMATION: Antibody C VH

<400> SEQUENCE: 5

```
gaggtgcagc tggtgcagtc tggggctgag gtgaagaaac ctggggccac agtgaaaatc    60
tcctgcaagg tttatggata catttttcacc gactacaaca tttactgggt gcgacaggcc   120
cctggaaaag ggcttgagtg gatgggactt attgatcctg acaatggtga cacattttac   180
gcagagaagt tccagggcag agccaccatg accgcggaca cgtcttcaga cagagcctac   240
atggaattga gcagcctgag atttgaggac acggccgtgt attattgtgc aacagtgatg   300
gggaagtgga tcaagggggg ctatgactac tggggccggg gcaccctggt caccgtctcc   360
tca                                                                  363
```

<210> SEQ ID NO 6
<211> LENGTH: 333
<212> TYPE: DNA
<213> ORGANISM: Homo sapiens
<220> FEATURE:
<223> OTHER INFORMATION: Antibody C VL

<400> SEQUENCE: 6

```
cagtctgtgc tgacgcagcc gccctcagtg tctggggccc cagggcagag ggtcaccatc    60
tcctgcactg ggagcagctc caacatcggg gcaggttatg atgtacactg gtatcagcaa   120
```

```
cttccaggaa cagcccccaa actcctcatc tatgataatt tcaatcggcc ctcagggqtc    180 cctgaccgat tctctggctc caagtctggc acctcagcct ccctggccat cactgggctc    240
caggctgaag atgaggctga ttattattgc cagtcctatg acagccccac cctcacctcc    300
cccttcggaa ccgggaccaa gctgaccgtc cta                                 333

<210> SEQ ID NO 7
<211> LENGTH: 366
<212> TYPE: DNA
<213> ORGANISM: Homo sapiens
<220> FEATURE:
<223> OTHER INFORMATION: Antibody D VH

<400> SEQUENCE: 7
caggtccagc tggtgcagtc tggggctgag gtgaagaagc ctggggcctc agtgaaggtc     60
tcctgcaagg cttctggtta cacctttaca aattatggtc tcagctgggt gcgacaggcc    120
cctggacaag gcttgagtg gatgggatgg atcagcgcta ataatggcga cacaaattat     180
ggacaggaat tccagggcag agtcaccatg accacagata catccacgag cacagcctac    240
atggagttga ggagcctgag atctgacgac acggccgttt attactgtgc gagagactcc    300
agcagcagct gggcccgctg gttttttcgat ctctgggggcc gggggacact ggtcaccgtc    360
tcctca                                                              366

<210> SEQ ID NO 8
<211> LENGTH: 327
<212> TYPE: DNA
<213> ORGANISM: Homo sapiens
<220> FEATURE:
<223> OTHER INFORMATION: Antibody D V

<400> SEQUENCE: 8
tcctatgtgc tgactcagcc accctcggtg tcagtggccc caggaaagac ggccaggatt     60
acctgtgggg gaaacatcat tggaagtaaa cttgtacact ggtaccagca gaagccaggc    120
caggcccctg tgctggtcat ctatgatgat ggcgaccggc cctcagggat ccctgagcga    180
ttctctggct ccaactctgg gaacacggcc accctgacca tcagcagggt cgaggccggg    240
gatgaggccg actattattg tcaggtgtgg gatactggta gtgatcccgt ggtattcggc    300
ggagggacca gctgaccgt cctaggt                                        327

<210> SEQ ID NO 9
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VH chain

<400> SEQUENCE: 9
gaggtgcagc tgttggagtc tgggggaggc ttggtacagc ctgggggqtc cctgagactc      60 tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gaaacccttg    300
tactactatg atgaacaata tggcgtagta tatgatgctt ttgtctgggg ccggggqgaca    360
```

```
ctggtcaccg tctcctca                                              378

<210> SEQ ID NO 10
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VL chain

<400> SEQUENCE: 10
cagtctgtgc tgacgcagcc gccctcagtg tctggggccc cagggcagag ggtcaccatc      60
tcctgcactg ggagcagctc caacatcggg gcaggttatg atgtacactg gtaccagcag     120
cttccaggga cagcccccaa gctcctcatc tatggtgaca cccatcggcc ctcagggatc     180
cctgaccgat tctctggctc caagtctggc acctcagcct ccctggccat cactgggctc     240
caggctgagg atgaggctga ttattactgc cagtcctatg acaccgtacg tctccaccat     300
gtgttcggcg agggaccaa gctgaccgtc ctaggt                               336

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agcctatggc agggatatcg t                                                21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cctgtaatct tgaccccagc                                                  20

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
aggctcacta ccgcgcctgc ttg                                              23

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggatgcgatt aaggaccttg tt                                               22
```

```
<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgtcaaagct gcacacagtc a                                              21

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
tgacaaagcc cgctcctacc tgca                                           24
```

CELLS FOR TRANSIENT EXPRESSION AND USES THEREOF

CROSS REFERENCE TO RELATED APPLICATIONS

This application is a National Stage Application of International Application No. PCT/EP2010/063583, filed Sep. 15, 2010, said International Application No. PCT/EP2010/063583 claims benefit of U.S. Provisional Application No. 61/242,478 filed Sep. 15, 2009. Each of the above listed applications is incorporated by reference herein in its entirety for all purposes.

REFERENCE TO THE SEQUENCE LISTING

This application incorporates by reference a Sequence Listing submitted with this application as text file entitled TRANS3US.txt created on May 8, 2012 and having a size of 14 kilobytes.

The present invention relates to an expression-enhanced cell line, a method of obtaining such a cell line, a method of producing exogenous polypeptides from such a cell line, and a kit related thereto. Such cell lines are particularly suitable for the transient expression of exogenous polypeptide.

Protein expression systems comprising the introduction of foreign DNA into eukaryotic host cells are the mainstay of biotechnology providing quantities of heterologous polypeptides for many purposes, such as proteins for research and proteins for therapeutic use. Transfection protocols can be categorized as designed to produce "transient" or "stable" expression of the foreign gene. The line of demarcation between these two types of outcome is the integration of the introduced DNA into the host genome, and cells into which foreign DNA has become integrated are generally referred to as "stably transformed". In contrast to stable transformation, transient expression of transfected DNA does not depend on the integration of foreign DNA into host cell chromosomes. Transient expression is the method of choice where a large number of samples are to be analysed within a short period of time; typically the cells can be harvested as early as 1 to 4 days after transfection and the resulting supernatants or lysates are assayed for expression of the target gene. Since transient transfection is a key technique for biotechnological experimentation, there is the continual need for improvements in transient transfection technology to provide increased yields of heterologous polypeptides.

Epstein Barr Virus (EBV) is a member of the herpesvirus family. In transformed primate B-lymphocyte cells, the ~170 kilobase pair EBV genome is maintained extra-chromosomally. Maintenance of the extra-chromosomal (episomal) genome is mediated by the interaction between the EBV nuclear antigen-1 (EBNA-1) protein and the EBV origin of replication (oriP) [1, 2]. OriP consists of two elements which are required for episomal plasmid replication, a family of repeats and a 65 bp dyad symmetry element [3]. Each of these elements contains a number of binding sites for the EBNA-1 protein [4]. In 1984, Yates et at identified a region on the EBV viral genome which allows recombinant plasmids carrying it to be maintained episomally in cells latently infected with EBV; they designated this region oriP, for Origin of Plasmid replication [1]. Since oriP only improves stability of plasmids in cells which express the EBV genome, they suggested that there must be a second trans-acting element within the EBV genome which interacts with the oriP. In 1985, the same group identified the trans-acting region, and mapped it to the part of the genome encoding EBNA-1 [2]. Plasmids which contain both oriP and the EBNA-1 gene will replicate autonomously in a variety of cultured cells, thought originally to include primate cell lines, but not rodent cell lines [2].

As well as permitting episomal replication, Saeki et al (1998) showed that plasmids containing the EBNA-1, oriP sequences and a gene of interest had a longer retention time in the nucleus of rodent cells compared to plasmids without the EBV sequences. In addition, transgene activity from the EBV-derived plasmids was higher than from the plasmids without the EBV sequences, suggesting that the EBV sequences may also have an enhancer function on transgene expression. The EBV plasmids showed increased nuclear retention and transgene activity in rodent cells, but did not show episomal replication. In contrast, replication as well as transgene enhancement was seen in human embryonic kidney 293 (HEK293) cells [5].

Cachianes et al, 1993 [6], demonstrated that both the EBNA-1 and the oriP elements must be present for an increase in transgene activity, which was confirmed in 1998 by Längle-Rouault et al [7]. In both cases, the groups used human host cells which stably express EBNA-1. Transgene expression after transient transfection was increased when the expression plasmid contained oriP. In contrast, EBNA-1-negative cell lines showed comparable transgene expression activity in the presence and absence of oriP, showing that both components of the system must be present in order for enhancement of expression to occur. In addition, they found that the oriP needed to be carried on the same vector as the gene of interest for an increase in transgene activity [6, 7].

In addition, Cachianes et al [6] showed that plasmids containing oriP and a selectable marker can be maintained episomally for long periods (up to 6 months) when they were transfected into a host cell which constitutively expressed EBNA-1 and were kept under selection. Transgenes encoded on the oriP-containing vectors were produced continuously as long as the episome remained in the host cell under selection; this was postulated as an alternative to stably-integrated vectors for long term protein production [6, 7].

Tomiyasu et at [8] investigated the interaction between EBNA-1 and oriP in a panel of rodent cells. As observed in the human cells used by Cachianes et at [6] and Längle-Rouault et at [7], they found that rodent cells transfected with the oriP and EBNA-1 showed higher transgene expression levels than those transfected without the EBV-derived components. Transgene expression declined more rapidly in rodent cells than in primate cells, suggesting that the EBV-derived plasmids were not replicating in the rodent cells. The increase in expression was suggested to be due to nuclear localisation and retention of the plasmid, and transcriptional up-regulation, mediated by the EBNA-1/oriP interaction.

Although the initial work by Yates et al [1, 2] showed that rodent cells were non-permissive for the autosomal replication of EBV-derived plasmids, in 1993 it was shown that EBV-derived vectors would replicate in some rodent cells if large fragments (>10 kbp) of mammalian DNA were added to the vectors [9]. However, in 2000, Mizuguchi et at [10] used transfection studies and Southern Blot analysis to show that in some rodent cells the addition of large mammalian DNA fragments was not necessary for replication of EBV-derived plasmids. CHO cells were amongst those tested however it was found that in CHO cells the co-expression of EBNA-1 and oriP did not result in episomal replication, although there was an enhancement of transgene activity.

The use of HEK293 cells transfected stably transfected with the EBNA-1 gene (HEK293 EBNA cells), in combination with oriP-containing vectors, for transient gene expression is widely reported [11, 12, 13, 14, 15] and in recent years, the use of Chinese Hamster Ovary (CHO) cells for transient gene expression has been more widely reported.

However, transient expression from CHO cells has generally been less productive than that seen in HEK293-EBNA cells [13]. Early papers reported productivities of 8 mg/L to 22 mg/L IgG [16, 17] using a PEI transfection method in CHO DG44 cells with vectors containing both the EBNA-1 and oriP genes [17].

Recently Liu et al found that the use of proprietary transfection reagents can give equivalently high yields (50-80 mg/L) in both HEK 293 and CHO cells [18].

In 2005, Kunaparaju et al described the development of an optimised transient expression system for CHO cells which was based on episomal replication and retention of transfected plasmid DNA [19]. The so-called Epi-CHO system consists of CHO-T cells, which constitutively expressed the Polyomavirus (Py) large T (LT) antigen, and an expression vector containing oriP and EBNA-1 as well as the Py origin of replication. The PyOri and PyLT elements were present to drive the autonomous replication of the plasmid while the EBV elements were present for their nuclear retention and transcriptional enhancer effects.

WO 2002/027005 (Bayer) reported an enhanced transfection system comprising an episomal maintenance system, a strong promoter/enhancer, a protein transactivation system and a DNA coding for a heterologous protein. The preferred cell lines were non-rodent because an oriP-containing plasmid is not thought to replicate efficiently and CHO cells lack cellular factors for the transactivation system.

WO2006/060769 (Xoma Technologies) presents recombinant expression vectors comprising a 3'UTR of an immunoglobulin light chain and an EBV origin of replication. Further exemplified are methods of producing a recombinant protein that involve the use of two vectors, where each vector encodes a different polypeptide gene and where second vector should be present in an amount of from 1.5 to 2.5 times more than the first vector, to maximise product yield WO 2007/048601 (Roche) described a method for using a rodent cell stably transformed to express the EBNA-1 protein, said cell then being transfected with an episome comprising a promoter, oriP, a 5'UTR, the coding sequence for a gene of interest, a 3' UTR and polyadenylation sequence and a selectable marker.

Glutamine synthetase (GS; EC 6.3.1.2, also known as γ-glutamyl:ammonia ligase) plays an essential role in nitrogen metabolism by catalyzing the ATP-dependent condensation of glutamate and ammonia to form glutamine. Some cell lines (such as NS0) do not produce GS and therefore have an absolute requirement for glutamine and do not grow in glutamine-free medium. For these cells, the GS gene can therefore be used as a selectable marker. For cell lines such as CHO which do produce endogenous GS, the glutamine synthetase can still be used as a selectable marker, but it is necessary to use a specific inhibitor of GS (e.g. methionine sulphoximine (MSX)) to inhibit the endogenous enzyme. In 1992, Birch et al described the use of the GS gene in glutamine-auxotrophic cells for the development of high productivity stable cell lines [20].

It is an object of the present invention to provide an improved transient expression system.

According to a first aspect of the present invention there is provided an expression-enhanced cell line derived from a parent cell line, the expression-enhanced cell line comprising nucleic acid encoding Epstein-Barr Virus Nuclear Antigen 1 or a functional derivative, analogue, or variant thereof; and further comprising:

(a) a nucleic acid encoding an exogenous glutamine synthetase;
(b) a nucleic acid encoding an endogenous glutamine synthetase, wherein the endogenous glutamine synthetase is arranged to have enhanced enzymatic activity and/or enhanced expression relative to the parent cell line under comparable conditions; or
(c) both (a) and (b).

Surprisingly, the inventors have found that a cell line expressing EBNA-1 together with glutamine synthetase, hereinafter referred to as an "expression-enhanced" cell line or cells, is capable of higher gene expression in a transient expression system than a cell line having EBNA-1 or glutamine synthetase alone. These expression-enhanced cells are capable of providing a transient expression system that is robust and scalable, regularly producing over 100 mg/L of heterologous polypeptide at all scales from 30 mL shaker flasks to 250 L single use bioreactors.

According to another aspect of the present invention, there is provided an expression-enhanced cell line transfected with Epstein-Barr Virus (EBV) Nuclear Antigen 1 (EBNA-1) and comprising an upregulated glutamine synthetase (GS).

The cell line can comprise nucleic acid encoding both an endogenous glutamine synthetase and an exogenous glutamine synthetase.

The nucleic acid encoding the glutamine synthetase is operably linked to a promoter and optionally an enhancer. The promoter can be an SV40 promoter. In one embodiment the expression-enhanced cell line is capable of expressing glutamine synthetase in an amount sufficient to allow growth of the cell in glutamine-free medium, and optionally further supplemented with MSX at a concentration of at least 1 nM, 10 nM, 100 nM, 1 µM, 2 µM, 3 µM, 5 µM, 10 µM, 20 µM, 50 µM, 200 µM, 1 mM, or 3 mM.

In one embodiment the expression-enhanced cell line has no endogenous glutamine synthetase enzymatic activity, or has no detectable endogenous glutamine synthetase enzymatic activity. In an alternative embodiment, the expression-enhanced cell line has a detectable endogenous glutamine synthetase enzymatic activity.

The nucleic acid encoding glutamine synthetase can be chromosomal. In an alternative embodiment, the nucleic acid encoding glutamine synthetase is episomal. The nucleic acid encoding EBNA-1 can be chromosomal. The nucleic acid encoding EBNA-1 can be episomal.

Providing chromosomally encoded glutamine synthetase and/or EBNA-1 advantageously provides a cell line having stably integrated nucleic acid encoding glutamine synthetase and/or EBNA-1. This can help to overcome difficulties associated with maintainence of episomal nucleic acid in cell lines.

In one embodiment the expression-enhanced cell line is transiently transfected with Epstein-Barr Virus (EBV) Nuclear Antigen 1 (EBNA-1) and transiently transfected with glutamine synthetase (GS). In another embodiment the expression-enhanced cell line is transiently transfected with Epstein-Barr Virus (EBV) Nuclear Antigen 1 (EBNA-1) and stably transfected with glutamine synthetase (GS). In another embodiment the expression-enhanced cell line is stably transfected with Epstein-Barr Virus (EBV) Nuclear Antigen 1 (EBNA-1) and transiently transfected with glutamine synthetase (GS). In another embodiment the Epstein-Barr Virus (EBV) Nuclear Antigen 1 (EBNA-1) and glutamine synthetase (GS) are both stably transfected in the expression-enhanced cell line. The Epstein-Barr Virus (EBV) Nuclear Antigen 1 (EBNA-1) and/or glutamine synthetase (GS) may be constitutively expressed in the expression-enhanced cell line.

In another embodiment the expression-enhanced cell line has an enhanced endogenous glutamine synthetase (GS) and is transiently transfected with Epstein-Barr Virus (EBV) Nuclear Antigen 1 (EBNA-1). In another embodiment the expression-enhanced cell line has enhanced endogenous glutamine synthetase (GS) and is stably transfected with Epstein-Barr Virus (EBV) Nuclear Antigen 1 (EBNA-1).

The expression-enhanced cell line can further comprise nucleic acid encoding an exogenous polypeptide (also known as a heterologous polypeptide). The nucleic acid encoding the exogenous polypeptide can be located trans relative to the nucleic acid encoding EBNA-1 and/or the nucleic acid encoding GS.

The nucleic acid encoding the exogenous polypeptide can further encode an EBNA-1 binding sequence. In one embodiment the EBNA-1 binding sequence is an EBV origin of replication (oriP), or functional variant thereof. A functional variant of oriP can comprise an oriP sequence having more or less than the normal 20 repeat sequences in the family of repeats (FR). A functional variant of oriP can comprise an oriP sequence having a split family of repeats (FR). For example, the repeat sequences of the family of repeats can be spaced in several distinct clusters in the nucleic acid sequence. Such variants of oriP are identified in Aiyar et al (2009) [28].

The exogenous polypeptide can comprise an antibody heavy chain and/or an antibody light chain, a $V_H$ or $V_L$ domain, or a fragment thereof. The exogenous polypeptide can be a prodrug, enzyme, enzyme fragment, enzyme inhibitor, enzyme activator, biologically active polypeptide, hedgehog protein, bone morphogenetic protein, growth factor, erythropoietin, thrombopoietin, G-CSF, interleukin, interferon, immunoglobulin, such as Fab, Fv, scFv, DAb immunoglobulin fragment, or combinations thereof. In one embodiment the exogenous polypeptide is an immunoglobulin or an immunoglobulin fragment.

The nucleic acid encoding the exogenous polypeptide can be episomal. The nucleic acid encoding the exogenous polypeptide can be a plasmid or viral nucleic acid. One or more selection markers can be provided on the nucleic acid encoding the exogenous polypeptide. In one embodiment the selection marker for the nucleic acid encoding the exogenous polypeptide is not a nucleic acid encoding a glutamine synthetase.

The nucleic acid encoding the exogenous polypeptide can comprise a 3' untranslated region (UTR) comprising a polyadenylation signal. The nucleic acid encoding the exogenous polypeptide can comprise a 5' region comprising a promoter.

In another aspect of the invention there is provided an expression-enhanced cell line expressing EBNA-1 and having an up-regulated GS, characterised in that said cell line contains an episome, wherein said episome comprises:
(a) a selection marker;
(b) an Epstein Bar Virus (EBV) origin of replication (oriP); and
(c) an expression cassette suitable for the expression of an exogenous polypeptide in said cell, wherein said expression cassette comprises a promoter sequence, a 5' untranslated region, a nucleic acid sequence encoding said exogenous polypeptide and a 3' untranslated region comprising a polyadenylation signal.

The invention also provides a method of obtaining an expression-enhanced cell line from a parental cell line, which comprises:

(a) providing a parental cell line; and
(b) transfecting the parental cell line with nucleic acid encoding Epstein-Barr Virus Nuclear Antigen 1, or a derivative, analogue, or variant thereof; and either
    (i) transfecting the parental cell line with exogenous nucleic acid encoding a glutamine synthetase; or
    (ii) adapting the cell line to enhance expression and/or enzymatic activity of an endogenous glutamine synthetase; or
    (iii) both (i) and (ii).

In a further embodiment of the invention, there is provided a method for obtaining an expression-enhanced cell line of the invention which comprises:
(a) providing a parental cell line; and
(b) transfecting said cell line with the EBNA-1 gene and the GS gene,
to produce an EBNA-1 and GS expressing cell; and
optionally transfecting said EBNA-1 and GS expressing cell line with a gene encoding an exogenous polypeptide.

In a further embodiment of the invention, there is provided a method for obtaining an expression-enhanced cell line of the invention which comprises:
(a) providing a parental cell line;
(b) transfecting said parental cell line with the EBNA-1 gene, and
(c) treating the cell line transfected with the EBNA-1 gene obtained in (b) to increase the expression and/or enzymatic activity of GS;
to produce a cell line transfected with EBNA-1 and comprising an upregulated GS.

For the avoidance of doubt, it would be clear to the skilled man that the EBNA-1 and GS genes could be transfected into the cell in sequential transfection reactions in any order or in the same transfection reaction.

The nucleic acid encoding Epstein-Barr Virus Nuclear Antigen 1 and the nucleic acid encoding a glutamine synthetase can be transfected into a cell on the same nucleic acid. The nucleic acid encoding Epstein-Barr Virus Nuclear Antigen 1 and the nucleic acid encoding a glutamine synthetase can be transfected on separate nucleic acids.

In a further aspect of the invention, there is provided a method for obtaining an expression-enhanced cell line of the invention which comprises:
(a) providing a parental cell line;
(b) transfecting said parental cell line with nucleic acid comprising an EBNA-1 gene, and
(c) treating the cell line to increase the expression and/or enzymatic activity of GS;
to produce a cell line transfected with EBNA-1 and comprising an upregulated GS;
and optionally transfecting said EBNA-1 and GS expressing cell with a nucleic acid comprising a gene encoding an exogenous polypeptide.

The skilled man would be familiar with methods to increase/enhance the expression and/or enzymatic activity of endogenous glutamine synthetase, for example, expression of GS can be increased/enhanced by a method selected from culturing the cells in the absence of glutamine or at a low level of glutamine, and optionally selecting for cells culturable in the presence of increasing concentrations of MSX; mutating the GS promoter; adding a stronger promoter relative to an endogenous GS promoter; mutating the endogenous GS enhancer; adding an enhancer; adding a stronger enhancer relative to an endogenous GS enhancer; and providing additional copies of the endogenous GS; or by a combination of such methods.

In a further aspect of the invention, there is provided a method for obtaining an expression-enhanced cell line of the invention which comprises:
(a) providing a parental cell;
(b) providing a first plasmid comprising:
   i. prokaryotic origin of replication;
   ii. a selection marker; and
   iii. a functional expression cassette for EBNA-1, whereby said expression cassette comprises a promoter sequence, a 5' untranslated region, a nucleic acid encoding EBNA-1 and a 3' untranslated sequence comprising a polyadenylation signal;
(c) providing a second plasmid comprising:
   i. a prokaryotic origin of replication;
   ii. a selection marker; and
   iii. a functional expression cassette for GS, whereby said expression cassette comprises a promoter sequence, a 5' untranslated region, a nucleic acid encoding GS and a 3' untranslated sequence comprising a polyadenylation signal;
(d) introducing said first and second plasmids into said cell and selecting a cell transfected with EBNA-1 and GS.
and optionally
(e) providing a third plasmid comprising
   i. a prokaryotic origin of replication;
   ii. a selection marker; and
   iii. a functional expression cassette for an exogenous polypeptide, whereby said expression cassette comprises a promoter sequence, a 5' untranslated region, a nucleic acid encoding said exogenous polypeptide and a 3' untranslated sequence comprising a polyadenylation signal; and
(f) introducing said third plasmid into said EBNA-1 and GS transfected cell and selecting a transformed cell expressing said exogenous polypeptide.

In a further aspect of the invention, there is provided a method for obtaining an expression-enhanced cell line of the invention which comprises:
(a) providing a parental cell;
(b) providing a first plasmid comprising:
   i. a prokaryotic origin of replication;
   ii. a selection marker;
   iii. a functional expression cassette for EBNA-1, whereby said expression cassette comprises a promoter sequence, a 5' untranslated region, a nucleic acid encoding EBNA-1 and a 3' untranslated sequence comprising a polyadenylation signal; and
   iv. a functional expression cassette for GS, whereby said expression cassette comprises a promoter sequence, a 5' untranslated region, a nucleic acid encoding GS and a 3' untranslated sequence comprising a polyadenylation signal; and
(c) introducing said first plasmid into said cell and selecting a cell transfected with EBNA-1 and GS;
and optionally
(d) providing a second plasmid comprising
   i. a prokaryotic origin of replication;
   ii. a selection marker; and
   iii. a functional expression cassette for an exogenous polypeptide, wherein said expression cassette comprises a promoter sequence, a 5' untranslated region, a nucleic acid encoding said exogenous polypeptide and a 3' untranslated sequence comprising a polyadenylation signal; and
(e) introducing said second plasmid into the EBNA-1 and GS transfected cell obtained in (c) and selecting a transfected cell expressing said exogenous polypeptide.

The skilled man would be familiar with a number of techniques to stably or transiently transfect a parental cell line with Epstein-Barr Virus (EBV) Nuclear Antigen 1 (EBNA-1) and glutamine synthetase (GS). In one embodiment a parental cell line is co-transfected with an expression vector encoding Epstein-Barr Virus (EBV) Nuclear Antigen 1 (EBNA-1) and an expression vector encoding glutamine synthetase (GS). In another embodiment a parental cell line is sequentially transfected, in any order, with an expression vector comprising Epstein-Barr Virus (EBV) Nuclear Antigen 1 (EBNA-1) and an expression vector encoding glutamine synthetase (GS). In one embodiment the expression vector encoding glutamine synthetase does not comprise nucleic acid encoding a polypeptide intended for expression and purification. In another embodiment a parental cell line is transfected with an expression vector comprising both Epstein-Barr Virus (EBV) Nuclear Antigen 1 (EBNA-1) and glutamine synthetase (GS), wherein the expression vector does not comprise nucleic acid encoding an exogenous polypeptide intended for expression and purification. The exogenous polypeptide intended for expression and purification can be selected from an immunoglobulin heavy and/or light chain, a $V_H$ or $V_L$ domain, or a fragment thereof, prodrugs, enzyme inhibitors, enzyme activators, hedgehog proteins, bone morphogenetic proteins, growth factors, erythropoietin, thrombopoietin, G-CSF, interleukins, interferons, immunoglobulin, and immunoglobulin fragments, such as a Fab, Fv, scFv, and DAb, or combinations thereof. In another embodiment the exogenous polypeptide intended for expression and purification comprises an enzyme or fragment thereof, wherein the enzyme is not glutamine synthetase.

Suitable expression vectors can be chosen or constructed, containing appropriate regulatory sequences, including promoter sequences, terminator sequences, polyadenylation sequences, enhancer sequences, marker genes and other sequences. Vectors can be plasmids, e.g., phagemid, or viral, e.g. 'phage, as appropriate [21]. Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. [22].

A number of expression vectors are available to the skilled man, such as episomal vectors, non-episomal vectors, vectors with inducible or constitutive expression cassettes, monocistronic or multi-cistronic vectors.

The method can comprise introducing nucleic acid, such as a vector, into a cell line. The introduction of nucleic acid can employ any suitable technique. For eukaryotic cells, suitable techniques can include calcium phosphate transfection, DEAE-Dextran, electroporation, liposome-mediated transfection, cationic polymers (e.g. polylysine and polyethyeneimine) and transduction using retrovirus or other virus, e.g., vaccinia or, for insect cells, baculovirus. Introducing nucleic acid in the host cell, in particular a eukaryotic cell can use a viral or a plasmid based system. The introduction can be followed by causing or allowing expression from the nucleic acid, e.g., by culturing host cells under conditions for expression of the gene. The purification of the expressed product can be achieved by methods known to one of skill in the art.

There are a number of reference works that the skilled man can refer to for transfection techniques. These include:
(i) J. Sambrook, E. F. Fritsch, and T. Maniatis, 1989, Molecular Cloning: A Laboratory Manual, Second Edition, Books 1-3, Cold Spring Harbor Laboratory Press;
(ii) Ausubel, F. M., ed., Current Protocols in Molecular Biology, Volumes I to III (1997);

(iii) Glover, N. D., and Hames, B. D., ed., DNA Cloning: A Practical Approach, Volumes I and II (1995), Oxford University Press;
(iv) Freshney, R. I. (ed.), Animal Cell Culture—a practical approach, IRL Press (1986);
(v) Watson, J. D., et al., Recombinant DNA, Second Edition, CHSL Press (1992);
(vi) Winnacker, E. L., From Genes to Clones; N.Y., VCH Publishers (1987);
(vii) Celis, J., ed., Cell Biology, Second Edition, Academic Press (1998);
(viii) Freshney, R. I., Culture of Animal Cells: A Manual of Basic Techniques, Second Edition, Alan R. Liss, Inc., N.Y. (1987);
(ix) B. Roe, J. Crabtree, and A. Kahn, 1996, DNA Isolation and Sequencing: Essential Techniques, John Wiley & Sons;
(x) J. M. Polak and James O'D. McGee, 1990, In Situ Hybridization: Principles and Practice; Oxford University Press;
(xi) M. J. Gait (Editor), 1984, Oligonucleotide Synthesis: A Practical Approach, IrI Press. Each of these general texts is herein incorporated by reference.

The present invention further provides a polypeptide expression system for the production of exogenous polypeptides using the expression-enhanced cell lines of the invention. The expression system is suitable for the production of, for example, prodrugs, enzymes, enzyme fragments, enzyme inhibitors, enzyme activators, biologically active polypeptides, hedgehog proteins, bone morphogenetic proteins, growth factors, erythropoietin, thrombopoietin, G-CSF, interleukins, interferons, immunoglobulins, immunoglobulin heavy and/or light chains, $V_H$ and/or $V_L$ domain, or fragments thereof, or immunoglobulin fragments such as Fab, Fv, scFv, and DAb. In one embodiment said exogenous polypeptide is an antibody or an antibody fragment.

In another aspect of the invention there is provided an exogenous polypeptide produced using an expression system of the invention. In one embodiment the exogenous polypeptide is formulated with a pharmaceutically acceptable excipient as a pharmaceutical composition.

In another aspect of the invention there is provided a protein expression system comprising an expression-enhanced cell line stably transfected with and constitutively expressing EBNA-1 and GS, transfected with an expression vector comprising a nucleic acid sequence encoding an exogenous polypeptide. In another embodiment of the invention there is provided an expression-enhanced cell line stably transfected with and constitutively expressing EBNA-1 and GS transfected with an expression vector comprising a nucleic acid sequence encoding an exogenous polypeptide. In another embodiment the exogenous polypeptide is selected from an immunoglobulin, an antibody heavy chain and/or an antibody light chain, a $V_H$ and/or $V_L$ domain, or a fragment thereof. In other embodiments of the invention there are provided expression-enhanced cell lines stably transfected with and constitutively expressing EBNA-1 and GS transfected with an expression vector comprising a nucleic acid sequence encoding an antibody heavy chain and/or an antibody light chain, a $V_H$ and/or $V_L$ domain, or a fragment thereof. The antibody heavy chain and an antibody light chains can be present on one vector or the antibody heavy chain on one expression vector and the antibody light chain on a different expression vector. The $V_H$ domain can be present on one expression vector and the $V_L$ domain on another expression vector.

In another aspect of the invention there is provided a polypeptide expression system comprising:
a) an expression-enhanced cell line constitutively expressing EBNA-1 and GS; and
b) an expression vector comprising an EBV origin of replication (oriP) and a gene encoding an exogenous polypeptide.

In another aspect of the invention there is provided a method of expressing an exogenous polypeptide from a cell line, wherein the method comprises;
a) providing an expression-enhanced cell line of the invention;
b) transfecting the cell line with an expression vector comprising an EBV origin of replication (oriP) and a gene encoding the exogenous polypeptide to form a transiently transfected host cell; and
c) culturing the transiently transfected cell under conditions suitable for the expression of the exogenous polypeptide, whereby the polypeptide is expressed.

According to another aspect of the invention, there is provided a method of producing an exogenous polypeptide from an expression-enhanced cell line according to the invention, comprising:
a) providing an expression-enhanced cell line according to the invention;
b) transfecting the cell line with an expression vector encoding an EBV origin of replication (oriP) and the exogenous polypeptide to form a transiently transfected host cell;
c) culturing the transiently transfected host cell to form an expressed exogenous polypeptide; and
d) isolating the expressed exogenous polypeptide from other cellular material.

Preferably, in embodiments described herein, culturing the transiently transfected host cell is performed under conditions suitable for the expression of the exogenous polypeptide.

In another aspect of the invention there is provided a method of making exogenous polypeptide comprising a method as described herein.

The method according to the invention is suited for the production of exogenous polypeptide, which can be a secreted exogenous polypeptide, at all scales of production from cell culture flasks to bioreactors and scalable disposable bioreactors. The method is suitable for production at large scale, i.e. industrially. The cultivation of a cell for the production of a desired polypeptide in large scale generally consists of a sequence of individual cultivations, wherein all cultivations except the final, i.e. the large scale, cultivation, i.e., the last one in the sequence, are performed until a certain cell density is reached in the culture vessel. If the predetermined cell density is reached the entire cultivation or a fraction thereof is used to inoculate the next cultivation vessel, which has a larger volume, up to 100 times the volume of the preceding cultivation. All cultivations, which serve as a basis for at least one further cultivation in a larger volume, are denoted as "seed train fermentation". Only in the large scale cultivation, i.e. in the cultivation which is not intended to serve as the basis for a further cultivation in a larger volume, which is also denoted as "main fermentation", is the endpoint of the cultivation determined depending on the concentration of the produced secreted exogenous immunoglobulin in the cultivation medium or the cultivation time. The term "large scale" as used within this application denotes the final cultivation of an industrial production process. In one embodiment a large scale cultivation is performed in a volume of at least 50 liters, in another embodiment of at least 500 liters, in a further embodiment of at least 1000 liters up to a volume of 2000 or 12,500 liters. In one embodiment the final, i.e. large scale, cultivation medium does not contain a eukaryotic selection agent.

In one embodiment the cultivation of said transfected cell line, such as a CHO cell line is performed in the presence of eukaryotic selection agent(s) in a volume of less than 500 liters and the cultivation of said transfected cell line is performed in the absence of eukaryotic selection agent(s) in a volume of 500 liters or more and the recovering of the exogenous polypeptide is from the cultivation medium without said eukaryotic selection agents. In a further embodiment the cultivation is comprising sequential cultivations with increasing cultivation volume up to a final cultivation volume, whereby the cultivations are performed in the presence of eukaryotic selection agent(s) up to a cultivation volume of 1% (v/v) of the cultivation volume of the final or main cultivation, and in the absence of all eukaryotic selection agents in a cultivation volume of more than 1% (v/v) of the cultivation volume of the final cultivation. In a further embodiment said cultivation comprises sequential seed train cultivations with increasing cultivation volume, whereby each of the seed train cultivations is performed in the presence of eukaryotic selection agent(s) and the main fermentation is performed in the absence of all eukaryotic selection agents. In one embodiment the cultivation of said transfected cell line is performed in the presence of eukaryotic selection agent(s) in the seed train fermentations and the cultivation of said transfected cell line is performed in the absence of eukaryotic selection agents in the main fermentation and the recovering of the exogenous polypeptide is from the main cultivation medium not containing eukaryotic selection agent(s). In these embodiments the eukaryotic selection agent(s) is(are) added during the seed train cultivations and omitted during the production phase (main fermentation culture) of said cell line. The term "production phase" denotes the cultivation of a cell line, such as a CHO cell line, in a large volume, i.e. the main fermentation, after which the produced exogenous polypeptide is recovered.

In one embodiment the exogenous polypeptide is a secreted exogenous immunoglobulin which can be a completely processed secreted exogenous immunoglobulin. The term "completely processed secreted exogenous immunoglobulin" denotes an immunoglobulin i) which is secreted to the cultivation medium and whose signal sequences has been cleaved, ii) which comprises an antigen binding region, iii) which has secondary modifications, such as attached saccharides or polysaccharides, and/or correctly formed disulfide bonds.

A cell usable for the large scale production of therapeutics, i.e., polypeptides intended for the use in humans, has to fulfill distinct criteria. Amongst others these are that it has to be cultivatable in serum-free medium, preferably animal-component-free medium (ACF). In one embodiment the polypeptide-free, chemical defined media is the CD CHO medium available from Invitrogen Corp.

In another embodiment of a method according to the invention is a method beginning with the first transfection and ending with the recovery of the exogenous polypeptide performed in the same medium. The term "in the same medium" denotes within the current application that beginning with the first transfection and ending with the recovery of the exogenous polypeptide from the main fermentation cultivation medium the same medium is used. This denotes that in all steps new medium of the same composition is employed. This does not denote that the same additives have to be added to the medium in all steps, i.e. the medium may be supplemented with different additive in different steps of the method. In one embodiment the medium used in the method according to the invention is the same medium in all steps and is a medium suitable for the large-scale production of the exogenous polypeptide.

The exogenous polypeptide can be recovered from supernatants or lysates using chromatographic methods. Therefore in one embodiment the method according to the invention comprises the final step of purifying said exogenous polypeptide with one or more chromatographic steps.

Chromatographic methods and their use are known to a person skilled in the art. See for example, Chromatography, 5 edition, Part A: Fundamentals and Techniques, Heftmann, E. (ed), Elsevier Science Publishing Company, New York, (1992); Advanced Chromatographic and Electromigration Methods in Biosciences, Deyl, Z. (ed.), Elsevier Science BV, Amsterdam, The Netherlands, (1998); Chromatography Today, Poole, C. F., and Poole, S. K., Elsevier Science Publishing Company, New York, (1991); Scopes, Protein Purification: Principles and Practice (1982).

For example, for the expression of an exogenous immunoglobulin the vector with which the cell line of the invention is transfected may comprise a nucleic acid conferring resistance to a eukaryotic selection agent, a nucleic acid encoding the light chain of said exogenous immunoglobulin and/or a nucleic acid encoding the heavy chain of said exogenous immunoglobulin. If the vector comprises only a nucleic acid encoding either the light chain of said immunoglobulin or the heavy chain of said immunoglobulin said CHO cell is also transfected in each step by another vector comprising a nucleic acid encoding the corresponding other chain of said immunoglobulin.

The invention further comprises a cell line of the invention cultivated in a polypeptide-free, chemical defined medium. Also encompassed is an exogenous polypeptide expressed from such a cell line. Another aspect of the current invention is a composition comprising the cell line of the invention.

In one embodiment of the invention the nucleic acid encoding glutamine synthetase is not used as a selection marker. For example, the ability of the cell line to grow and/or survive in the presence of MSX may not be used as a selection marker for nucleic acid encoding glutamine synthetase.

The parental cell line is preferably mammalian. Mammalian parental cell lines can be selected from a human cell line and a non-human cell line. Human cell lines can be selected from any suitable human cell line such as HEK (Human Embryonic Kidney), HeLa (Henrietta Lacks), Crucell's PER.C6® cell line, and human embryonic retina cells. Non-human cell lines can be selected from any suitable non-human cell line such as a rodent cell line and a primate cell line. Primate cell lines can be selected from any suitable primate cell line such as, COS (SV40 transformed African Green Monkey kidney cells).

The mammalian parental cell line can be a rodent cell line. The rodent cell line can be selected from any suitable rodent cell line such as, CHO (Chinese Hamster Ovary) cells or derivatives thereof, NS0 cells or derivatives thereof (ECACC 85110503), BHK (baby hamster kidney) cells or derivatives thereof, YB2/0 rat myeloma cells or derivatives thereof and mouse fibroblast cell lines such as NIH3T3 or derivatives thereof. CHO cell lines can include any of the group comprising CHO-K1 (ATCC CCL 61) [23], CHO-DXBI1, CHO-DG44, CHO-T and CHO-S.

Parental cells suitable for the invention can further comprise cell lines that produce proteins with modified or engineered glycosylation profiles, such as but not limited to cell lines that produce a-fucosylated antibodies for increased ADCC activity, e.g. CHO FUT-8 knockout cell lines (e.g. Biowa CHO FUT-8).

The parental cell line can be the Chinese hamster ovary (CHO) cell line ("CAT-S") as deposited with the European Collection of Cell Cultures (ECACC) under accession number 10090201.

According to another aspect of the present invention, there is provided a kit for exogenous polypeptide expression comprising:
a) an expression-enhanced cell line according to the invention; and
b) an expression vector comprising an EBV origin of replication (oriP) and nucleic acid encoding an exogenous polypeptide relative to the cell line.

The kit can further comprise instructions according to a method of the invention.

As used herein the term "antibody" refers to an oligoclonal, a polyclonal antibody, a monoclonal antibody, a chimeric antibody, a CDR-grafted antibody, a multi-specific antibody, a bi-specific antibody, a catalytic antibody, a chimeric antibody, a humanized antibody, a fully human antibody or an anti-idiotypic antibody and antibodies that can be labeled in soluble or bound form as well as fragments, variants or derivatives thereof including histidine-tagged derivatives, either alone or in combination with other amino acid sequences provided by known techniques. An antibody can be from any species. The term antibody can also include binding fragments of the antibodies of the invention; exemplary fragments include Fv, Fab, Fab', Fd, single stranded antibody (svFC), dimeric variable region (Diabody) and disulphide stabilized variable region (dsFv). In general, for the preparation of monoclonal antibodies or their functional fragments, especially of murine origin, it is possible to refer to techniques which are described in particular in the manual "Antibodies" [24] or to the technique of preparation from hybridomas described by Köhler and Milstein [25]. Antibody molecules and methods for their construction and use are also described in Holliger & Hudson [26].

As used herein the term 'cell culture' refers to cells growing in suspension or adherent, in roller bottles, flasks, glass or stainless steel cultivations vessels, and the like. Large scale approaches, such as bioreactors, are also encompassed by the term 'cell culture'. Cell culture procedures for both large and small-scale production of polypeptides are encompassed by the present invention. Procedures including, but not limited to, a fluidized bed bioreactor, shaker flask culture, disposable bioreactor or stirred tank bioreactor system can be used and operated alternatively in a batch, split-batch, fed-batch, or perfusion mode.

As used herein the terms 'cell culture medium' and 'culture medium' as used interchangeably within the current invention refer to a nutrient solution used for growing mammalian cells. Such a nutrient solution generally includes various factors necessary for growth and maintenance of the cellular environment. For example, a typical nutrient solution can include a basal media formulation, various supplements depending on the cultivation type and, occasionally, selection agents.

As used herein, the term "chemical defined medium" denotes a medium comprising only synthetic compounds and which is animal derived component free. Additionally the term "chemical defined medium" can denote a medium which contains in one embodiment less than 0.1 mM glutamine, in another embodiment less than 0.01 mM glutamine and in a further embodiment less than 0.001 mM glutamine. In one embodiment the chemical defined medium is free of glutamine. In one embodiment the chemical defined medium is free of animal derived components and also free of cell hydrolysates of plant origin. Exemplary synthetic chemically defined media are the CD CHO medium from Invitrogen.

As used herein the term 'EBNA-1 gene' or 'EBNA-1 nucleic acid' refers to the Epstein-Barr Virus (EBV) Nuclear Antigen 1 (EBNA-1) as defined by sequence NCBI accession number YP_401677. The term 'EBNA-1 gene' also refers to any variants of the EBNA-1 gene, which facilitate expression from an expression vector comprising an oriP element. A functional derivative, analogue, or variant of EBNA-1 may comprise a truncated, but functional, form of EBNA-1. A functional truncated form of EBNA-1 is described in WO2009/137911 A1. For example, a truncated form of EBNA-1 may be without the usual Gly-Ala repeats of the normal 641 amino acid full length protein. A functional derivative, analogue, or variant of EBNA-1 may comprise a peptide having at least 50%, 60%, 70%, 80%, 90%, 95% or 98% sequence identity over the full length of the EBNA-1 of SEQ ID NO: 1, or over the length of a truncated form of EBNA-1.

As used herein the term 'upregulated glutamine synthetase' may include the transfection of one or more glutamine synthetase genes into a cell, or an enhanced endogenous glutamine synthetase. Enhanced endogenous glutamine synthetase may comprise increased gene copy number of the endogenous glutamine synthetase, such that the cell line is capable of producing more glutamine synthetase. Additionally, or alternatively, the enzymatic activity of the endogenous glutamine synthetase may be enhanced. Such enhancement of enzymatic activity of the glutamine synthetase may be relative to the natural enzymatic activity of the endogenous glutamine synthetase under comparable conditions in vivo and/or in vitro.

As used herein the term "enhanced endogenous glutamine synthetase" refers to an increase in the protein level and/or an increase in the activity of endogenous glutamine synthetase in a cell. Such protein level and/or activity may be measured relative to the protein level and/or activity of a parental cell prior to enhancement.

As used herein the term 'enhancer' refers to a polynucleotide sequence that enhances transcription of a gene or coding sequence to which it is operably linked. Unlike promoters, enhancers are relatively orientation and position independent and have been found 5' or 3' (Lusky, M., et al., Mol. Cell Bio., 3 (1983) 1108-1122) to the transcription unit, within an intron (Banerji, J., et al., Cell, 33 (1983) 729-740) as well as within the coding sequence itself (Osborne, T. F., et al., Mol. Cell Bio., 4 (1984) 1293-1305). Therefore, enhancers may be placed upstream or downstream from the transcription initiation site or at considerable distances from the promoter, although in practice enhancers may overlap physically and functionally with promoters. A large number of enhancers, from a variety of different sources are well known in the art (and identified in databases such as GenBank) and are available as or within cloned polynucleotide sequences (from, e.g., depositories such as the ATCC as well as other commercial or individual sources). A number of polynucleotides comprising promoter sequences (such as the commonly-used CMV promoter) also comprise enhancer sequences. For example, all of the strong promoters listed above may also contain strong enhancers (see e.g. Bendig, M., M., Genetic Engineering 7 (Academic Press, 1988) 91-127).

As used herein the term 'expression' refers to transcription and/or translation processes occurring within a cell. The level of transcription of a nucleic acid sequence of interest in a cell can be determined on the basis of the amount of corresponding mRNA that is present in the cell. For example, mRNA transcribed from a sequence of interest can be quantitated by RT-PCR or by Northern hybridization [21]. Polypeptides encoded by a nucleic acid of interest can be quantitated by various methods, e.g. by ELISA, by assaying for the biological activity of the polypeptide, or by employing assays that are independent of such activity, such as Western blotting or radioimmunoassay, using immunoglobulins that recognize and bind to the polypeptide (see Sambrook, et al., 1989, supra).

As used herein the term 'expression cassette' refers to a construct that contains the necessary regulatory elements, such as promoter and polyadenylation site, for expression of at least the contained nucleic acid in a cell.

As used herein the term 'expression vector' refers to a nucleic acid (also denoted as nucleic acid molecule) providing all required elements for the expression of a polypeptide, for example EBNA-1 and/or GS or a heterologous polypeptide in a host cell. An expression vector comprises a prokaryotic plasmid propagation unit, e.g. for E. coli, in turn comprising a prokaryotic origin of replication, and a nucleic acid conferring resistance to a prokaryotic selection agent, further comprises the expression vector one or more nucleic acid(s) conferring resistance to an eukaryotic selection agent, and one or more nucleic acid encoding a polypeptide. Preferably the nucleic acids conferring resistance to a selection agent and the nucleic acid(s) encoding a polypeptide are each placed within an expression cassette, whereby each expression cassette comprises a promoter, a coding nucleic acid, and a transcription terminator including a polyadenylation signal. Gene expression is usually placed under the control of a promoter, and such a structural gene is said to be "operably linked to" the promoter. Similarly, a regulatory element and a core promoter are operably linked if the regulatory element modulates the activity of the core promoter.

As used herein the term 'glutamine synthetase (GS)' refers to an enzyme which catalyzing the ATP-dependent condensation of glutamate and ammonia to form glutamine which is known under the enzyme classification system as EC 6.3.1.2. For example, as defined by sequence NCBI accession number X03495, and/or as defined by SEQ ID NO: 2: Glutamine synthetase is also known as γ-glutamyl:ammonia ligase. The term 'glutamine synthetase' also refers to any variants of the glutamine synthetase (GS) enzyme, which facilitate the biosynthesis of glutamine from glutamate and ammonia.

As used herein the term 'exogenous nucleic acid' refers to a nucleic acid or a population of nucleic acid molecules, that do not exist naturally within a given host cell. The term may be used interchangeably with 'heterologous nucleic acid'. Nucleic acid molecules exogenous/heterologous to a particular host cell may contain nucleic acid derived from the host cell species (i.e. endogenous nucleic acid) so long as that host nucleic acid is combined with non-host nucleic acid (i.e. exogenous nucleic acid). For example, a nucleic acid molecule containing a non-host nucleic acid segment encoding a polypeptide operably linked to a host nucleic acid segment comprising a promoter is considered to be a heterologous nucleic acid molecule. Conversely, a heterologous nucleic acid molecule can comprise an endogenous structural gene operably linked with an exogenous promoter. A peptide or polypeptide encoded by a non-host nucleic acid molecule is a "heterologous" or "exogenous" peptide or polypeptide.

As used herein the term 'heterologous polypeptide' denotes a polypeptide, which is not naturally (i.e. endogenously) produced by the mammalian cell or the host cell. The term 'heterologous polypeptide' may be used interchangeably with the term 'exogenous polypeptide'. The polypeptide produced according to the method of the invention is produced by recombinant means. Such methods are widely known in the state of the art and comprise protein expression in eukaryotic cells with subsequent recovery and isolation of the heterologous polypeptide, and usually purification to a pharmaceutically acceptable purity. For the production, i.e. expression, of a polypeptide one or more nucleic acid(s) encoding the polypeptide is/are inserted each into an expression cassette by standard methods. Hybridoma cells can, e.g., serve as a source of such nucleic acids encoding antibody light and heavy chains. The expression cassettes may be inserted into an expression plasmid(s), which is (are) then transfected into host cells, which do not otherwise produce the heterologous polypeptide. Expression is performed in appropriate eukaryotic host cells and the polypeptide is recovered from the cells after lysis or from the culture supernatant.

As used herein the term 'isolated' refers to a nucleic acid or a polypeptide that is essentially free from contaminating cellular components, such as carbohydrate, lipid, other proteinaceous impurities or other nucleic acids associated with the nucleic acid or polypeptide in nature. Typically, a preparation of isolated polypeptide or nucleic acid contains the polypeptide or nucleic acid in a highly purified form, i.e. at least about 80% pure, at least about 90% pure, at least about 95% pure, greater than 95% pure, or greater than 99% pure. Polypeptides and nucleic acid may be formulated with diluents or adjuvants and still for practical purposes be isolated. Polypeptides may be glycosylated, either naturally or by systems of heterologous eukaryotic cells (e.g. CHO or NS0 (ECACC 85110503)) cells, or they may be (for example if produced by expression in a prokaryotic cell) unglycosylated.

As used herein the phrase "a nucleic acid conferring resistance to a selection agent" refers to a nucleic acid that allows cells carrying it to be specifically selected for or against, in the presence of a selection agent. Such a nucleic acid is also denoted as selection marker. Typically, a selection marker will confer resistance to a selection agent (drug) or compensate for a metabolic or catabolic defect in the host cell. A selection marker can be positive, negative, or bifunctional. A useful positive selection marker is an antibiotic resistance gene. This selection marker allows cells transformed therewith to be positively selected for in the presence of the corresponding selection agent, i.e. under selected growth in the presence e.g. of the corresponding antibiotic. A non-transformed cell is not capable to grow or survive under the selective growth conditions, i.e. in the presence of the selection agent, in culture. Positive selection markers allow selection for cells carrying the marker, whereas negative selection markers allow cells carrying the marker to be selectively eliminated. Eukaryotic selection markers include, e.g., the genes for aminoglycoside phosphotransferase (APH) (conferring resistance to the selection agents such as e.g. hygromycin (hyg), neomycin (neomycin phosphotransferase II, neo), and G418), dihydrofolate reductase (DHFR) (conferring resistance to the selection agent methotrexate), thymidine kinase (tk), asparagine synthetase, tryptophan synthetase (conferring resistance to the selection agent indole), histidinol dehydrogenase (conferring resistance to the selection agent histidinol D), cytidine deaminase, adenosine deaminase and nucleic acids conferring resistance to puromycin, bleomycin, phleomycin, chloramphenicol, Zeocin, and mycophenolic acid. Further selection marker nucleic acids are reported e.g. in WO 92/08796 and WO 94/28143. Prokaryotic selection markers include, e.g. the beta-lactamase gene (conferring resistance to the selection agent ampicillin).

As used herein the term 'production protein' refers to a protein whose nucleic acid sequence has been transfected into a cell line to produce quantities of said protein.

As used herein the term 'promoter' refers to a polynucleotide sequence that controls transcription of a gene/structural gene or nucleic acid sequence to which it is operably linked. A promoter includes signals for RNA polymerase binding and transcription initiation. The promoter(s) used will be functional in the cell type of the host cell in which expression of the selected sequence is contemplated. A large number of promoters including constitutive, inducible and repressible promoters from a variety of different sources, are well known in the art (and identified in databases such as GenBank) and are available as or within cloned polynucleotides (from, e.g., depositories such as ATCC as well as other commercial or individual sources). A "promoter" comprises a nucleotide sequence that directs the transcription of an operably linked structural gene. Typically, a promoter is located in the 5' non-coding or untranslated region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee, R. E., et al., MoI. Endocrinol. 7 (1993) 551-560), cyclic AMP response elements (CREs), serum response elements (SREs; Treisman, R., Seminars in Cancer Biol. 1 (1990) 47-58), glucocorticoid response elements (GREs), and binding sites for other transcription factors, such as CRE/ATF (O'Reilly, M. A., et al., J. Biol. Chem. 267 (1992) 19938-19943), AP2 (Ye, J., et al., J. Biol. Chem. 269 (1994) 25728-25734), SP1, cAMP response element binding protein (CREB; Loeken, M. R., Gene Expr. 3 (1993) 253-264) and octamer factors (see, in general, Watson et al., eds., Molecular Biology of the Gene, 4th ed. (The Benjamin/Cummings Publishing Company, Inc. 1987), and Lemaigre, F. P. and Rousseau, G. G., Biochem. J. 303 (1994) 1-14). Among the eukaryotic promoters that have been identified as strong promoters for high-level expression are the SV40 early promoter, adenovirus major late promoter, mouse metallothionein-I promoter, Rous sarcoma virus long terminal repeat, Chinese hamster elongation factor 1 alpha (CHEF-I, see e.g. U.S. Pat. No. 5,888,809), human EF-1 alpha, ubiquitin, and human cytomegalovirus immediate early promoter (CMV IE). The "promoter" can be constitutive or inducible. An enhancer (i.e., a cis-acting DNA element that acts on a promoter to increase transcription) may be necessary to function in conjunction with the promoter to increase the level of expression obtained with a promoter alone, and may be included as a transcriptional regulatory element. Often, the polynucleotide segment containing the promoter will include enhancer sequences as well (e.g., CMV or SV40).

As used herein the term "transient transfection" as used within this application refers to a process in which the nucleic acid introduced into a cell is not required to integrate into the genome or chromosomal DNA of that cell. It is in fact predominantly maintained as an extrachromosomal element, e.g. as an episome, in the cell. Transcription processes of the nucleic acid of the episome are not affected and e.g. a protein encoded by the nucleic acid of the episome is produced.

As used herein the term "chromosomal" or "chromosomally" is an indication of the location of nucleic acid as part of the chromosome of a cell. This includes heterologous/exogenous nucleic acid sequences that are not of chromosomal origin, but are now integrated as part of the chromosome. The term "episomal" or "episomally" is an indication of the location of nucleic acid as part of the episome of a cell. This includes heterologous/exogenous nucleic acid sequences that are not of episomal origin.

As used herein the term "trans", as used in relation to the relative location of nucleic acid, refers to a nucleic acid sequence that is in a different location to another nucleic acid sequence. For example, the nucleic acid sequence is considered "trans" if it is located on a different nucleic acid molecule or vector relative to another nucleic acid sequence. A nucleic acid sequence located on a vector is considered "trans" to a nucleic acid molecule sequence on the chromosome. In contrast, the term "cis" refers to a nucleic acid sequence that is located on the same nucleic acid molecule, vector, or chromosome.

As used herein the term "stably transformed", "stably transfected", or "stable expression" as used within this application refers to a heritable and stable integration of exogenous nucleic acid into a host cell genome/chromosome.

As used herein, the terms "transformed" or "transfected" may encompass the term "transduced".

As used herein the term "transiently transformed", "transiently transfected" or "transient expression" refers to the provision of exogenous nucleic acid in a cell that is not stably integrated into the genome/chromosome of a host cell. The exogenous nucleic acid may be only temporarily-heritable or non-heritable. An example of transient transfection is a vector that is transfected into the cell, but does not chromosomally integrate, and may further require selective pressure in order to maintain it in the cell host for a period of time (for example 1-5, or 2-3 days).

The skilled person will appreciate that features of any one embodiment or aspect of the invention may be applied, where appropriate, to other embodiments or aspects of the invention.

The invention will now be exemplified by the following non-limiting examples in which the following abbreviations are used:
CMV Cytomegalo Virus
DNA Deoxyribo Nucleic Acid
EBNA-1 Epstein Ban-Virus Nuclear Antigen-1
EBV Epstein Barr Virus
ELISA Enzyme-Linked ImmunoSorbent Assay
GS Glutamine Synthetase
HPLC High Performance Liquid Chromatography
IgG Immunoglobulin G
M-PBST Powdered skimmed milk dissolved in PBST
MSX Methionine Sulfoximine
NEO Neomycin
PA-HPLC Protein A-HPLC
PEI polyethylenimine
PBS Phosphate Buffered Saline
PBS-T Phosphate Buffered Saline plus Tween
RNA Ribo Nucleic Acid
SDS-PAGE Sodium Dodecyl Sulphate-PolyAcrylamide Gel Electrophoresis
TMB 3,3',5,5'-Tetramethylbenzidine

In which the y-axis in the titre in mg/ml and the x-axis shows the different transfectants. Transfectants were transiently transfected to assess IgG productivity of the CHO- EBNA-1 transfectants. Wild type CHO cells (untransfected host cells) were included as a control. The highest producing transfectant was C1, with a titre by ELISA of 28 mg/L of MAb D. The bars show the average of two replicates, with the range indicated by the error bars.

Figure 1:
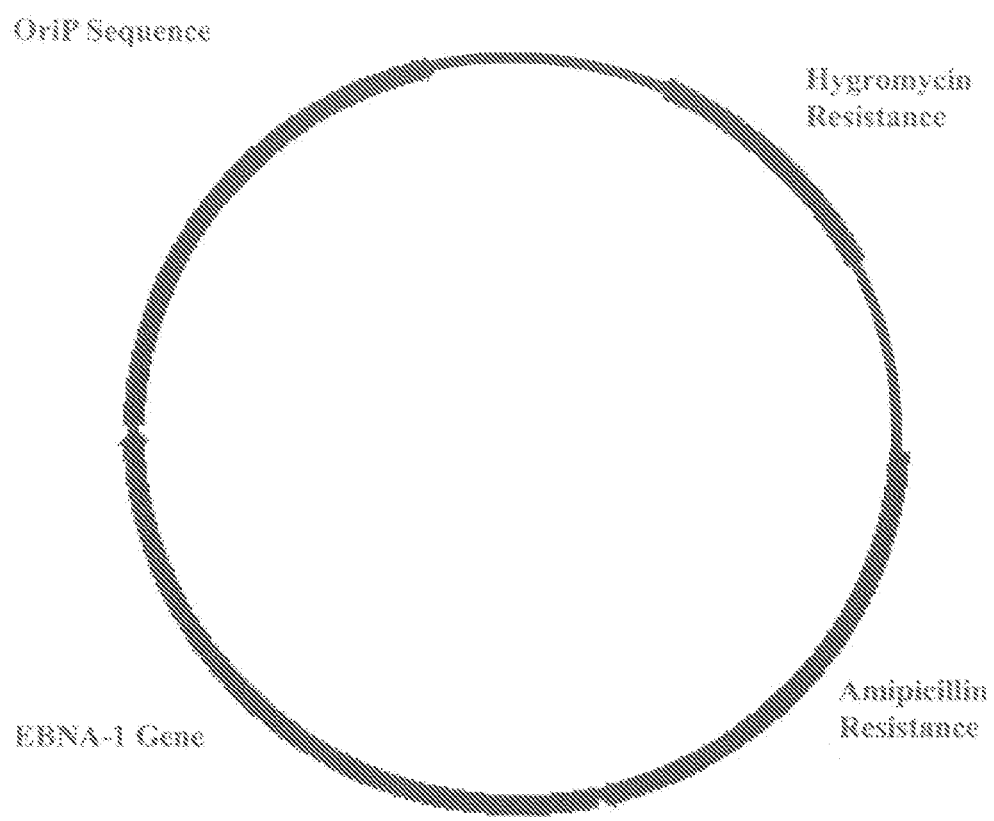
FIG. 1 pmCEP4 cloning vector
FIG. 2 pSI-GS cloning vector
FIG. 3 pEU expression vector for antibody heavy chain.
Figure 2:
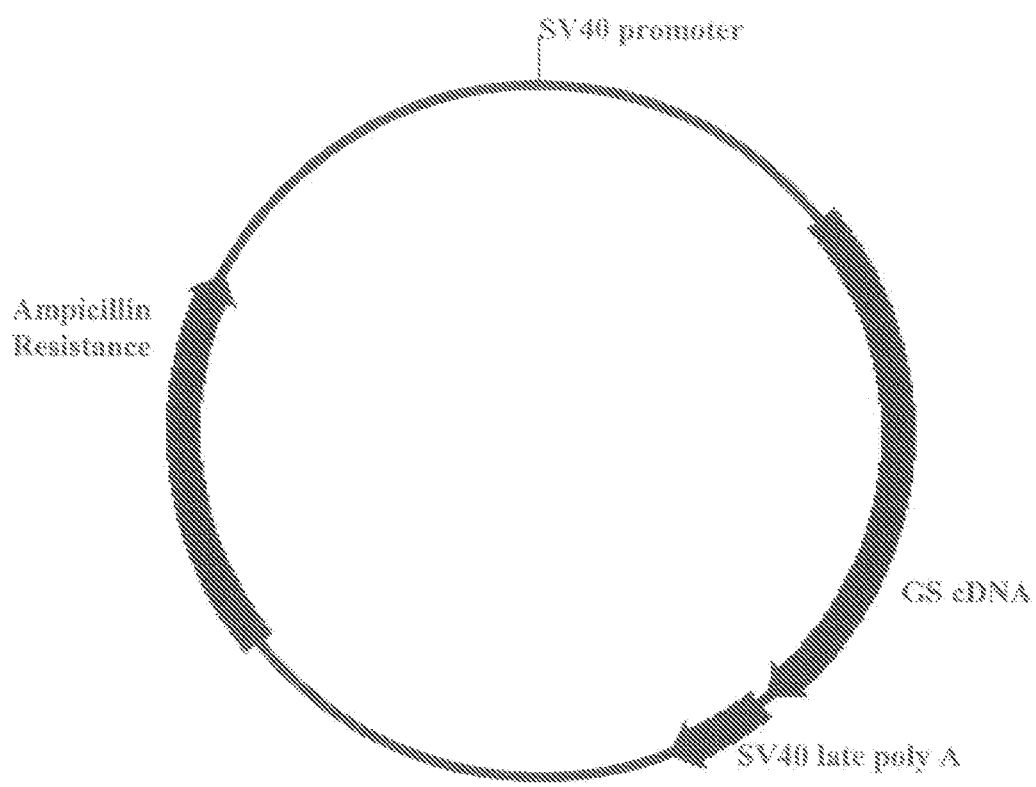
Figure 3:
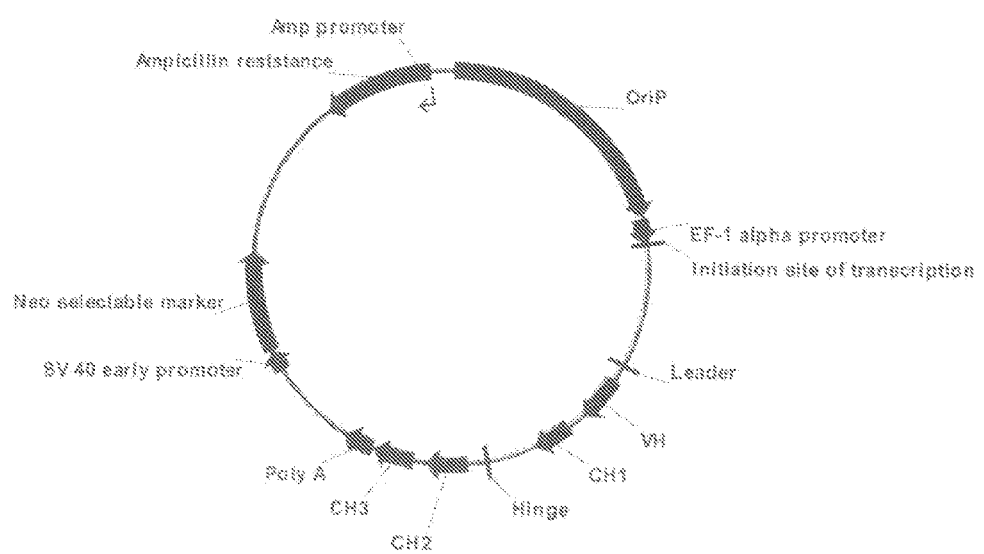
Figure 4:
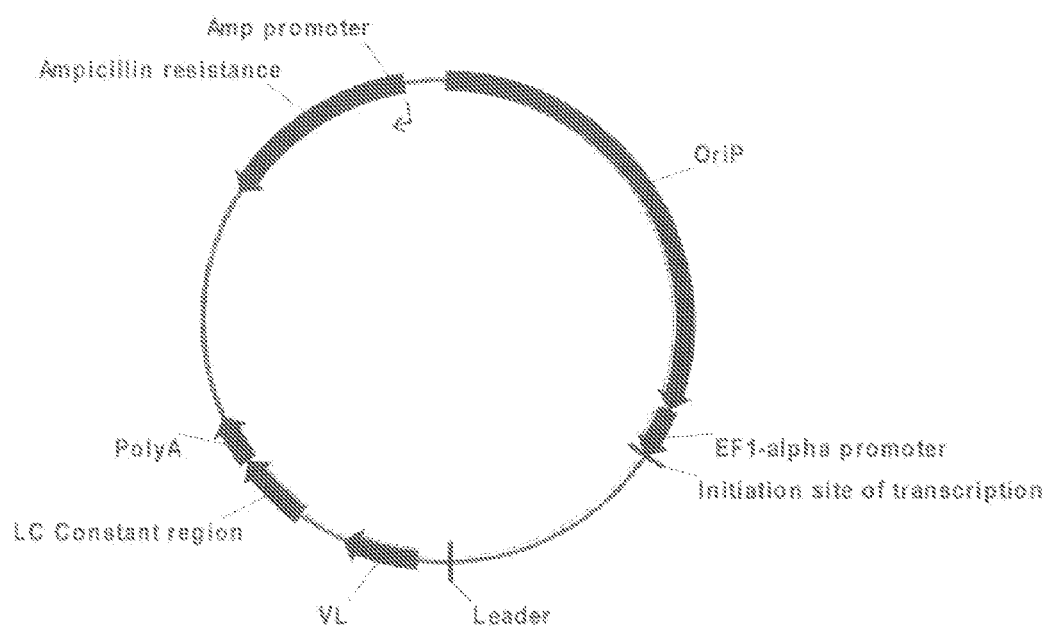
FIG. 4 pEU expression vector for antibody light chain.
Figure 5:
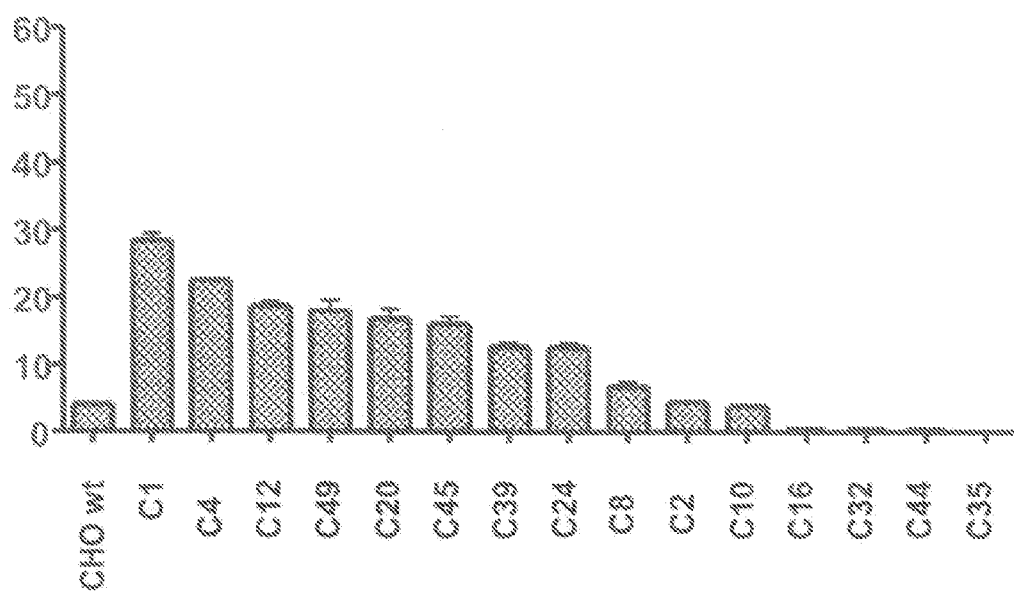
FIG. 5 Productivity distribution of CHO-EBNA-1 transfectants.
Figure 6:
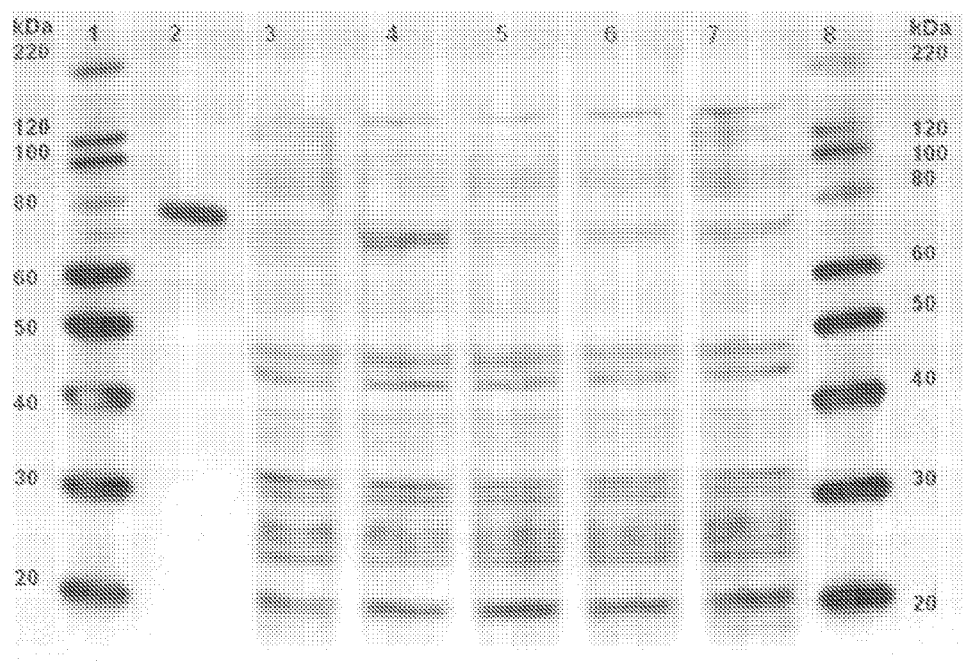

FIG. 6 Western blot of transfected cell lines showing EBNA-1 expression Lane 1 and 8 are Magic Mark protein standards (Invitrogen, UK). Lane 2 is the EBNA protein standard (Autogen Bioclear). Lane 3 is the CATS host cell line. Lane 4 is G22, Lane 5 is C1, Lane 6 is GH5 and Lane 7 is C1GS. A band which co-migrates at the same level as one of the minor bands in the EBNA standard lane can be detected in lanes 4-7 but not in lane 3, the CATS lane. CATS cell lines contain no transfected EBNA-1 whilst the G22, C1, GH5 and C1GS cell lines all contain transfected EBNA-1.

Figure 7:
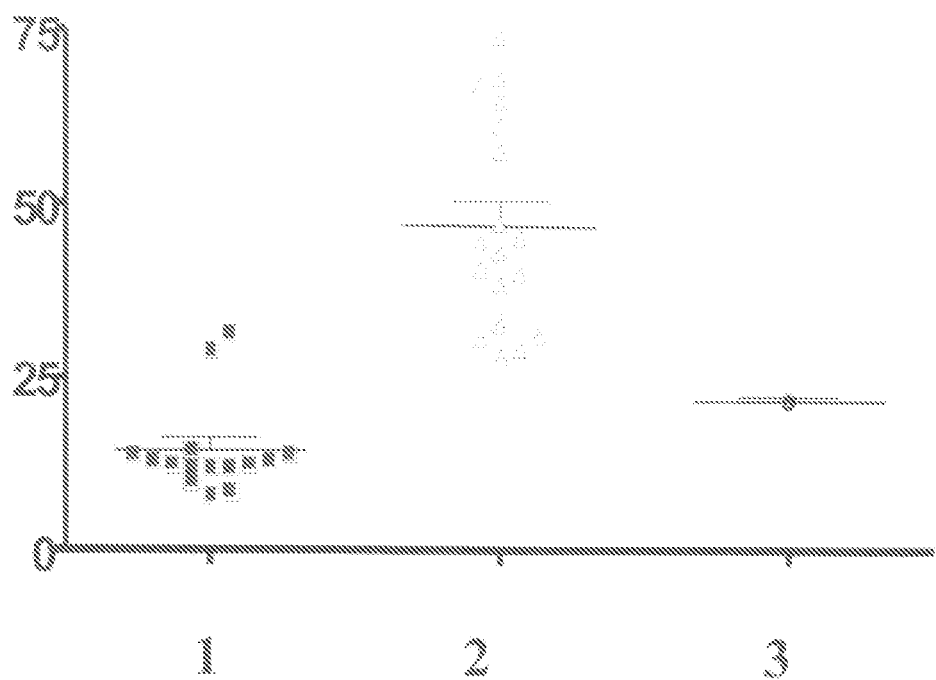

FIG. 7 Transient expression in different variants of C1 host cells in which the y-axis shows IgG titre in mg/l and the group 1 on the x-axis is the C1 clones, group 2 is the C1+GS transfectants and group 3 is the C1-parent. Distribution of transient transfection harvest titres for C1 clones and C1-GS transfectants. Fifteen C1 clones derived by limiting dilution cloning of C1 and 20 C1+GS transfectants derived by transfecting C1 with GS gene were transiently transfected with MAb A. The C1 parent cell line (heterogeneous population) was also transfected as a control. The bar shows the mean titre of the population while the dots show the distribution of titres within the population. For the C1 transfected with GS, the mean is significantly higher than the C1 parent or the C1 dilution clones and the distribution of the transfectants shows a shift in the population towards higher expression levels. Since the only difference between the populations is that the transfectants contain and are selected for the GS gene, the marked improvement in titre can be attributed to the stable co-expression of GS in the EBNA-1 expressing cell lines.

Figure 8:
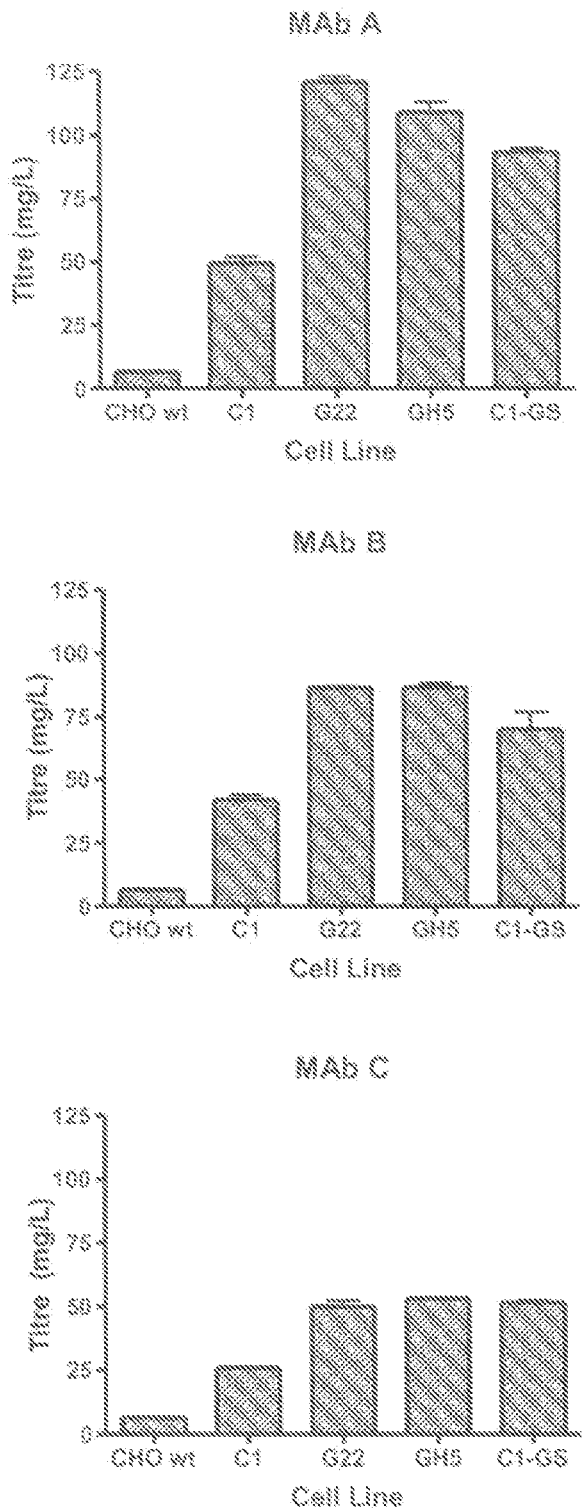

FIG. 8 Transient expression of antibody from a panel of CHO-EBNA-1/GS cells Expression of three different antibodies (MAb-A, B and C) from the lead CHO-EBNA-1/GS cell lines (G22, GH5 and C1-GS). These cell lines, and also including as control the host CHO cells (CATS) and CHO-EBNA (C1), were transiently co-transfected with light chain and heavy chain expression constructs for the appropriate antibodies. Cultures were allowed to over-grow and then clarified culture supernatants were analysed by Protein A HPLC to determine the concentration of antibody produced. Consistently for all three antibodies expressed, stable co-expression of both EBNA-1 and GS lead to higher transient expression of antibody in these cell lines relative to host cells stably expressing just EBNA-1 or neither EBNA-1 or GS.

Figures 9, 10:
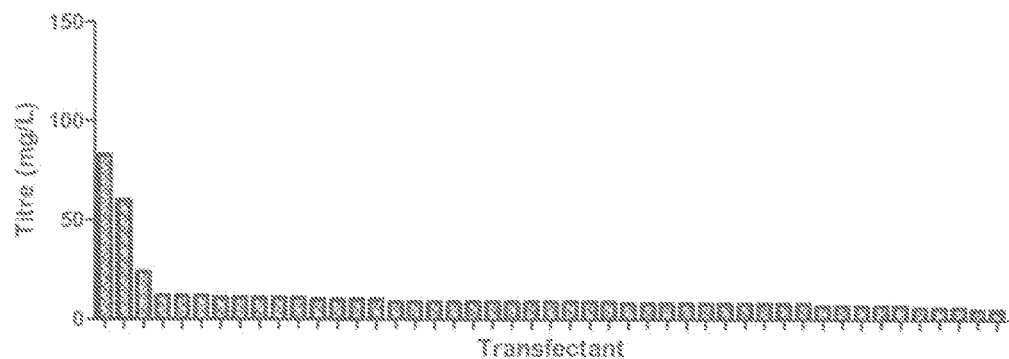

FIG. 9 Productivity distribution of CHO-EBNA-1 transfectants. Transfectants were transiently transfected in Culti-Flasks to assess IgG productivity of the CHO-EBNA-1-GS transfectants. The highest producing transfectant was CEP27, with a titre by PA-HPLC of 83 mg/L of MAb A.

FIG. 10 Productivity distribution of CHO-EBNA-1/GS transfectants selected using MSX and hygromycin. Transfectants were transiently transfected to assess IgG productivity of the CHO-EBNA-1 transfectants. The highest producing transfectant was CO16, with a titre of 113 mg/L by PA-HPLC of MAb A.

Figure 11:
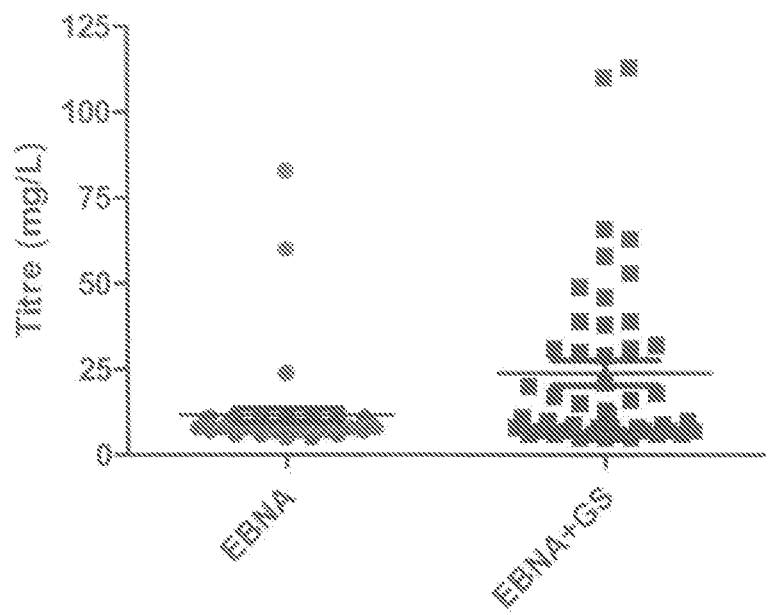

FIG. 11 Comparison of productivity distribution of CHO-EBNA-1 transfectants selected using hygromycin and CHO-EBNA-GS transfectants selected using MSX and hygromycin. Transfectants were transiently transfected to assess IgG productivity of the CHO-EBNA-1 transfectants. Analytical comparison of the two populations using a two-tailed t-test shows that the difference between the populations is highly significant (P<0.0001). Two-way ANOVA shows significance in the difference between populations (P=0.0066) but not within populations (P=0.6719).

Figure 12:
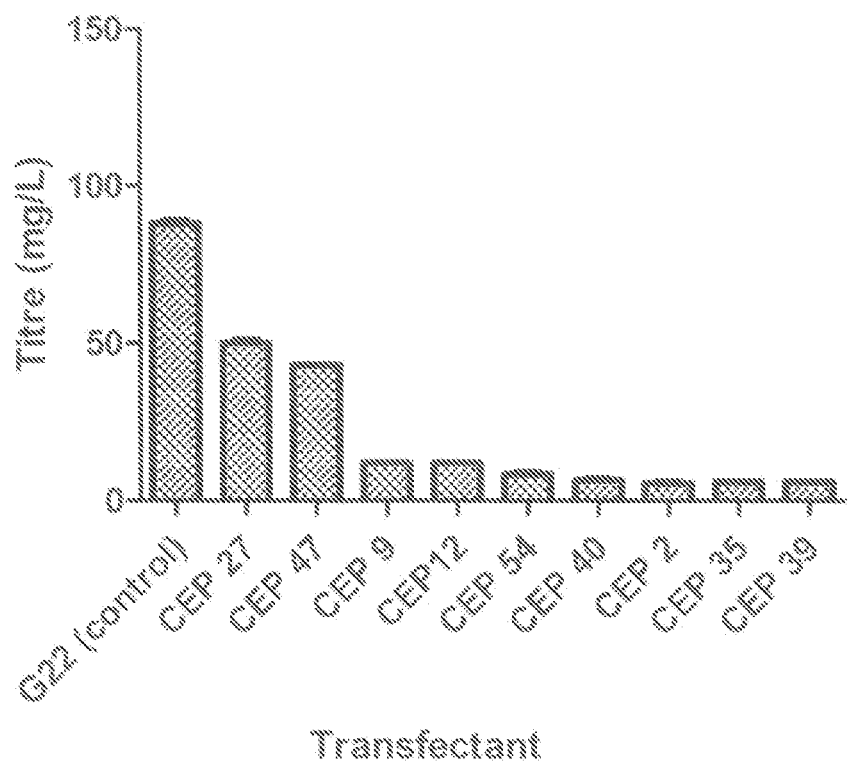

FIG. 12 Comparison of productivity distribution of CHO-EBNA-1 transfectants. Transfectants were transiently transfected to assess IgG productivity. G22 was included as a control to allow comparison between this round and the initial round of transfectant selection.

Figure 13:
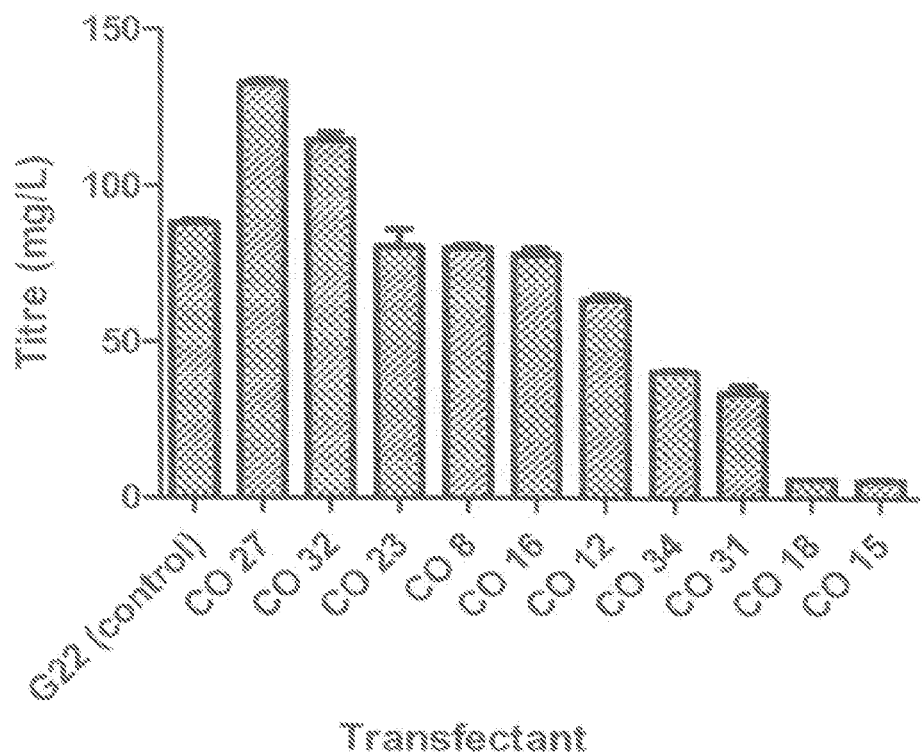

FIG. 13 Comparison of productivity distribution of CHO-EBNA-1-GS transfectants. Transfectants were transiently transfected to assess IgG productivity. G22 was included as a control to allow comparison between this round and the initial round of transfectant selection.

Figure 14:
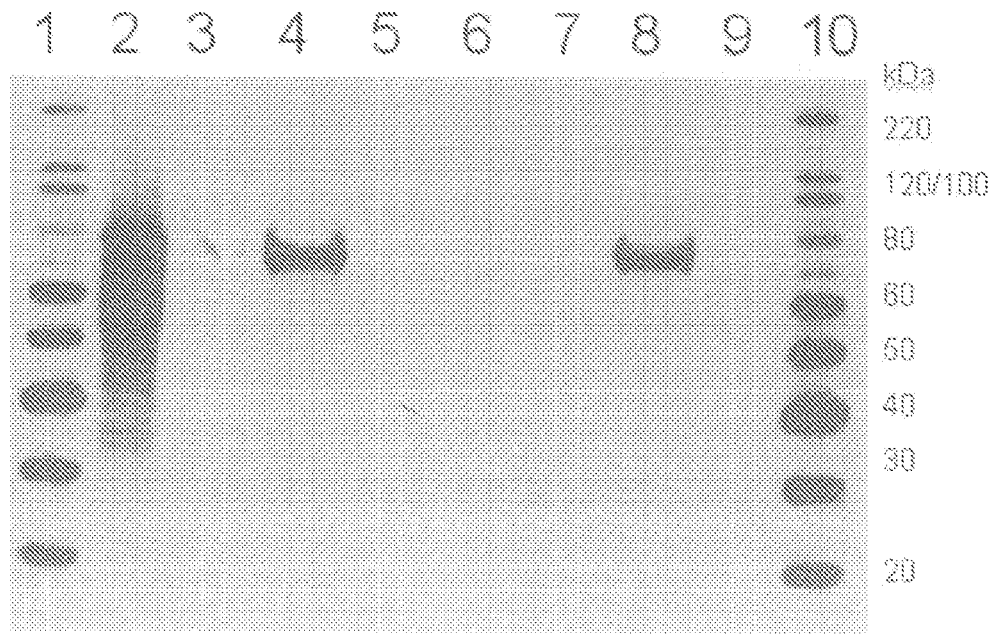

FIG. 14 Western Blot (Gel 1) of CHO-EBNA-1 transfectants. Lane 1—Magic Mark protein standard (Invitrogen), lane 2—EBNA-1 standard, Lane 3—CATS negative control, Lane 4—G22 positive control, Lane 5—CEP2 Lane 6—CEP9, Lane 7—CEP12, Lane 8—CEP27, Lane 9—CEP35, Lane 10—Magic Mark protein standard. CEP27 is the only (non-control) lane with EBNA-1 present. This confirms that EBNA-1 presence is required for high expression of antibody.

Figure 15:
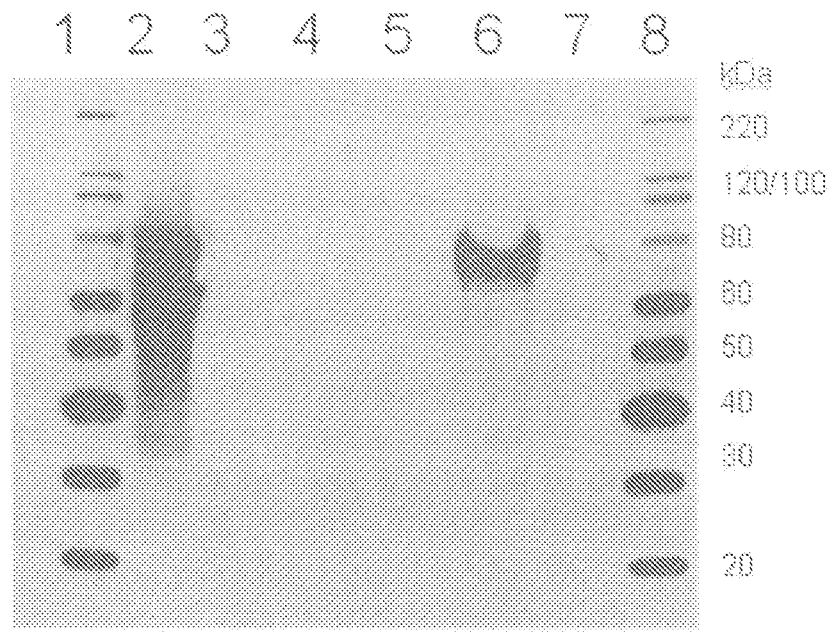

FIG. 15 Western Blot (Gel 2) of CHO-EBNA-1 transfectants. Lane 1—Magic Mark protein standard (Invitrogen), lane 2—EBNA-1 standard, Lane 3—CATS negative control, Lane 4—CEP39, Lane 5—CEP40, Lane 6—CEP47, Lane 7—CEP54 Lane 8—Magic Mark protein standard. CEP47 is the only (non-control) lane with EBNA-1 present. This confirms that EBNA-1 presence is required for high expression of antibody.

Figure 16:
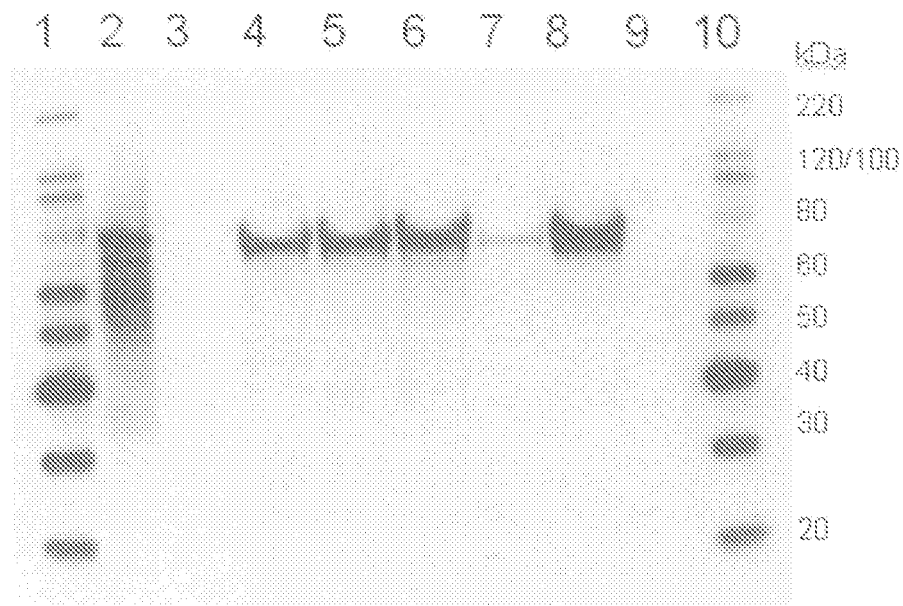

FIG. 16 Western Blot (Gel 1) of CHO-EBNA-1-GS transfectants. Lane 1—Magic Mark protein standard (Invitrogen), lane 2—EBNA-1 standard, Lane 3—CATS negative control, Lane 4—G22 positive control, Lane 5—CO8, Lane 6—CO12, Lane 7—CO15, Lane 8—CO16, Lane 9—CO18, Lane 10—Magic Mark protein standard. When there is little or no EBNA-1 present (lanes 7 and 9), the productivity of antibody is low. Higher antibody levels are seen from the transfectants which express EBNA-1.

Figure 17:
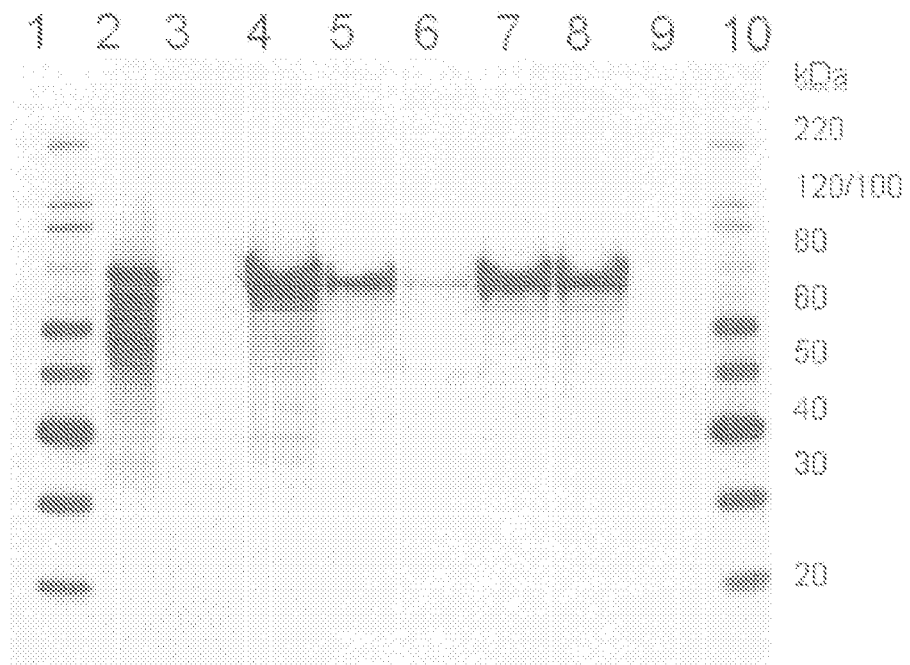

FIG. 17 Western Blot (Gel 2) of CHO-EBNA-1-transfectants. Lane 1—Magic Mark protein standard (Invitrogen), lane 2—EBNA-1 standard, Lane 3—CATS negative control, Lane 4—CO23, Lane 5—CO27, Lane 6—CO31, Lane 7—CO32, Lane 8—CO34, Lane 9—CO35, Lane 10—Magic Mark protein standard. When there is little or no EBNA-1 present (lanes 6 and 9), the productivity of antibody is low. Higher antibody levels are seen from the transfectants which express EBNA-1.

Figure 18:
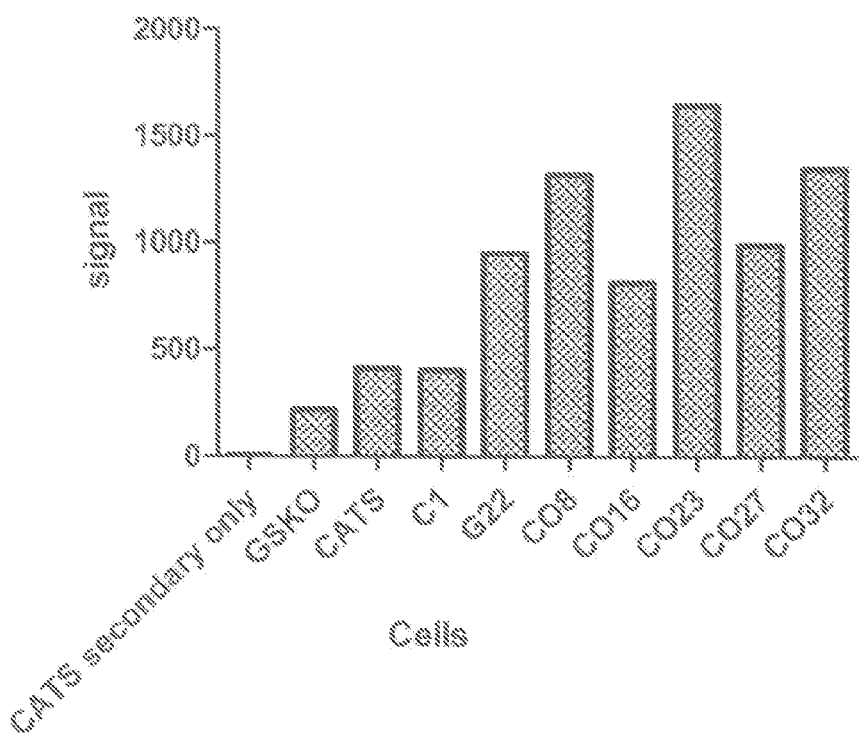

FIG. 18 The geometric means of the fluorescence peaks from flow cytometric analysis of GS in the different cell types is shown. The secondary only cells give the background levels of signal, and are used to set the cytometer up. The GSKO cells show the signal from a cell line with the endogenous GS knocked out. CATS signal is due to endogenous GS only. The signal from C1 (transfected with EBNA-1 only in the first round of selections) is comparable with CATS, indicating endogenous GS expression only. For G22 (included as a positive control) and for the five high-expressing co-transfected cell lines, the signal is much higher than for the endogenous GS only. This shows that we do have transfected GS expression in these cells.

Figure 19:
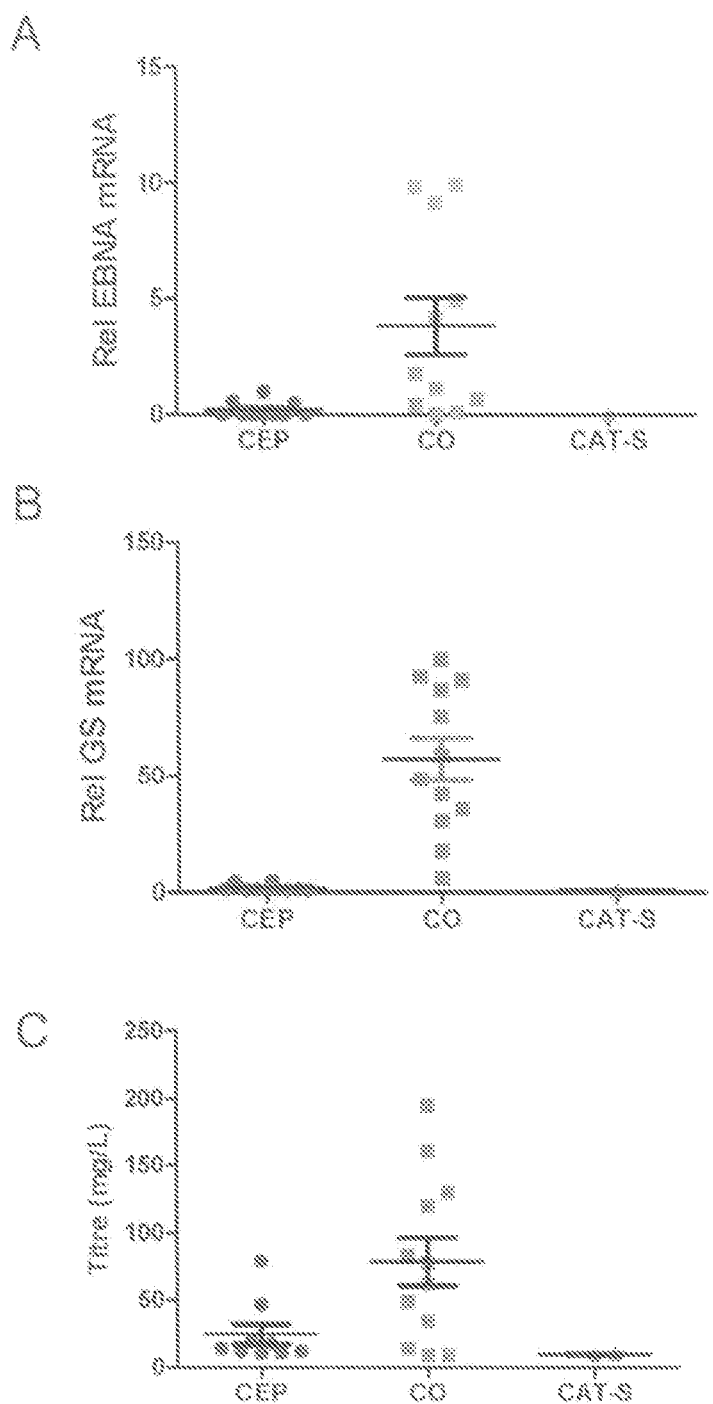

FIG. 19 qRT-PCR Characterisation of EBNA-1 and EBNA-1/GS transfected CHO Cells. A: The relative EBNA-1 mRNA ($\Delta\Delta$Ct) for 9* CEP (CHO EBNA-1), 12* CO (CHO EBNA-1/GS) and WT CAT-S are shown. All samples are normalised with GAPDH as a loading control and then expressed relative as fold difference to the C1 (CHO CAT-S/EBNA-1) cell line. As expected no EBNA-1 message was observed in the WT un-transfected CAT-S cell line, and a low level of variation of mRNA levels was observed with the CEP (CHO EBNA-1 only) cell lines. With Co (CHO EBNA-1/GS) cell lines a greater spread of relative EBNA-1 mRNA was observed with up to 10 fold greater levels of EBNA-1 than in the C1 (CHO CAT-S/EBNA-1) cell line.

B: The relative GS mRNA (ΔΔCt) for 9* CEP (CHO EBNA-1), 12* CO(CHO EBNA-1/GS) and WT CHO CAT-S are shown. All samples are normalised with GAPDH as a loading control and then expressed relative as fold difference to the C1 (CAT-S/EBNA-1) cell line. As expected very little GS mRNA was observed with the CEP (CHO EBNA-1 only) and WT CHO CAT-S cell line. However, with CO (CHO EBNA-1/GS) cell lines a large spread of relative GS mRNA levels were observed, ranging from 6 to 100 fold increases over the C1 (CHO CAT-S/EBNA-1) cell line.

C: Comparison of productivity distribution for 9* CEP (CHO EBNA-1), 12* CO (CHO EBNA-1/GS) and WT CHO CAT-S are shown. Cell lines were transiently transfected to assess IgG productivity of the CEP (CHO-EBNA-1) or CO (CHO-EBNA/GS) cell lines.

For all data sets the mean and the standard error of the mean (SEM) is shown.

BRIEF DESCRIPTION OF THE SEQUENCE LISTING

| Sequence ID No. | Identity | |
|---|---|---|
| 1 | EBNA-1 | Protein |
| 2 | GS | Nucleic Acid |
| 3 | MAb A $V_H$ Domain | Nucleic Acid |
| 4 | MAb A $V_L$ Domain | Nucleic Acid |
| 9 | MAb B $V_H$ Domain | Nucleic Acid |
| 10 | MAb B $V_L$ Domain | Nucleic Acid |
| 5 | MAb C $V_H$ Domain | Nucleic Acid |
| 6 | MAb C $V_L$ Domain | Nucleic Acid |
| 7 | MAb D $V_H$ Domain | Nucleic Acid |
| 8 | MAb D $V_L$ Domain | Nucleic Acid |

Materials a. Construction of Expression Plasmids

The expression vectors used for transient transfection are based on vectors known as pEU vectors (Persic et al, 1997) [27] The pEU vectors contain an expression cassette for the gene of interest, the Epstein Barr Virus (EBV) origin of replication (oriP) and a selectable marker for selection of stable transfectants. The selectable marker for amplification of the plasmid in E. coli is the ampicillin resistance gene.

The secretory leader sequence was derived from the mouse heavy chain sequence, and the encoding DNA sequence contains an intron. Downstream of the leader sequence is a polylinker with multiple cloning sites and then the antibody constant regions. There is a pEU vector for each antibody isotype. The variable region is cloned into the polylinker between the secretion leader sequence and the constant domain, in the appropriate vector. Transcription is driven from the EF-1α promoter and terminated by a poly A sequence.

The EBV origin of replication, oriP, was cloned as an EcoRI fragment into the pEU vector. The oriP is believed to interact with EBNA-1 protein to enhance productivity possibly by mediating episomal replication of the expression plasmid or/and through enhancing nuclear transport.

b. Construction of EBNA Vector (pmCEP4)

The pCEP4 plasmid was obtained from Invitrogen (Paisley, UK). The CMV promoter expression cassette was removed using digestion with XbaI and SalI. A new polylinker was made by annealing sequence specific coding and non-coding strand synthetic oligonucleotides. This was inserted into the pCEP4 vector backbone without the CMV promoter to generate the pmCEP4 vector.

c. Construction of GS Vector pSI-GS

The Glutamine Synthetase (GS) gene was obtained by RT-PCR amplification of hamster tissue RNA with primers designed based on the GS gene sequence from the NCBI database. The PCR product was then sub-cloned into a commercially available expression vector pSI (from Promega, Southampton, UK) containing the SV40 enhancer/early promoter and SV40 late poly A.

d. Construction of pEU Expression Vector for Antibody Heavy Chain

The cassette vector for the pEU heavy chain contains an expression cassette for the gene of interest, the EBV origin of replication (oriP) and a NEO selectable marker. The selectable marker for amplification of the plasmid in E. coli is the ampicillin resistance gene. Transcription is driven by the EF-1 alpha promoter and terminated by a poly-A signal. To construct expression vectors, the variable region is subcloned into the VH polylinker multiple cloning site.

e. pEU Expression Vector for Antibody Light Chain

The cassette vector for the pEU light chain contains an expression cassette for the gene of interest and the EBV origin of replication (oriP). The selectable marker for amplification of the plasmid in E. coli is the ampicillin resistance gene. Transcription is driven by the EF-1 alpha promoter and terminated by a poly-A signal. To construct expression vectors, the variable region is subcloned into the VL polylinker multiple cloning site. The vector was modified to remove a xanthan guanine phosphoribosyltransferase (XGPRT) selection marker.

f. Source and Derivation of CHO Cells

CHO.K1 cell line was obtained from ECACC No: 85051005. Adherent cell culture of CHOK1 was adapted to suspension cell culture using CD-CHO medium supplemented with 6 mM glutamine (Invitrogen, Paisley, UK).

EXAMPLE 1

General Techniques a) Recombinant DNA Techniques

Standard methods were used to manipulate DNA as described in Sambrook, J., Fritsch, E. F. and Maniatis, T. (1989), Molecular Cloning: A Laboratory Manual. Cold Spring Harbour Laboratory Press.

Molecular kits and biological reagents were used according to the manufacturers' instructions.

b) DNA Sequence Determination

DNA sequences were determined by double strand sequencing using Big Dye® V3.1 fluorescent chemistry according to the manufacturer's recommendations (Amersham Pharmacia Biotech, Little Chalfont, UK). Reactions were analysed using an ABI 3700 DNA analyser capillary sequencer (Applied Bio systems, Warrington, UK). Data from the sequence chromatograms was automatically compiled by the DNA analyser to generate DNA sequence information. The sequences from each individual sequencing reaction were compared and aligned to a reference sequence using Sequencher™ version 4.5 (Gene Codes Corporation, Ann Arbor, Mich., USA). Areas of sequence ambiguity were checked manually against sequence reaction chromatograms.

Big Dye® uses fluorescent DNA sequencing dye terminator chemistry in which different colour fluorescent dyes are attached to the ddNTPs (Dideoxyribonucleotides). BigDye® terminators utilize single energy transfer molecules, which include an energy donor and acceptor dye connected by a highly efficient energy transfer linker. In the structure of the BigDye® molecule, the acceptor is a dichlororhodamine dye. An energy transfer linker couples the donor fluorescein and acceptor dRhodamine dyes for efficient energy transfer in a single dye molecule.

c) DNA and Protein Sequence Analysis and Sequence Data Management

DNA sequence modelling was performed using MacVector v7.2.3 (Accelrys Software Inc, San Diego, Calif.). DNA sequence alignment was performed using Sequencher (Gene Codes Corporation, Ann Arbor, Mich.).

d) Cell Culture Techniques

Standard cell culture techniques were used. CHO cells were maintained in serum-free CD-CHO medium supplemented with 6 mM L-glutamine (Invitrogen, Paisley, UK). Stably transfected cells were maintained in CD-CHO supplemented with methionine sulfoximine (MSX; Sigma-Aldrich, Dorset, UK) and/or hygromycin (Invitrogen, Paisley, UK). For multi-well plates and T25 flasks cultures were incubated in a humidified incubator at 36.5° C., 5% $CO_2$.

For shaking cultures in vented Erlenmeyer flasks, cultures were incubated in a humidified incubator at 36.5° C., 5% $CO_2$, 140 rpm. Cells were split back to $2 \times 10^5$ viable cells/ml every 3-4 days in CD-CHO medium (Invitrogen, Paisley, UK) CD-CHO supplemented with methionine sulfoximine (MSX; Sigma-Aldrich, Dorset, UK) and/or hygromycin (Invitrogen, Paisley, UK).

e) Stable Transfection of Host Cells.

Linearised DNA was introduced into host cells by electroporation using Bio-Rad "GenePulser". Cells were plated in 96-well plates in non-selective medium and allowed to recover overnight before adding selective medium.

After 3-4 weeks, plates were examined to identify single colonies.

f) Transient Transfection of CHO and CHO-EBNA-1/CHO-EBNA-1-GS Cells to Assess Productivity of Cell Lines.

For transient transfections, cells from the continuous subculture were seeded at $5 \times 10^5$ viable cells/mL in maintenance medium. After 24 hours, cells in shaking cultures should be at $0.9\text{-}1.2 \times 10^6$ viable cells/mL. Cells were transiently co-transfected with antibody heavy chain vector and antibody light chain vector using transfection reagents such as 25 kDa linear PEI.

The antibodies used were:
MAb A (human IgG γ1-λ)
MAb B (human IgG γ2-λ)
MAb C (human IgG γ1-λ)
MAb D (human IgG γ4-λ)

After co-transfection, flasks were incubated in a humidified incubator at 36.5° C., 5% $CO_2$, 140 rpm.

For fed cultures, a concentrated nutrient feed was added as bolus additions over the course of the culture.

Every 2-4 days throughout the culture life, a sample of cells was removed and the cell density was counted as described above to determine cell density and viability. Once the viability of the culture fell to <30%, the overgrow was deemed to be complete. Clarified supernatant was stored at −70° C. until it was assayed by ELISA, Protein A-HPLC or Octet as described below.

The sequences of the variable domains of the above antibodies are listed in the accompanying sequence listing as follows:

| Antibody | Domain | Sequence |
|---|---|---|
| MAb A | $V_H$ | Seq ID No. 3 |
| | $V_L$ | Seq ID No. 4 |
| MAb B | $V_H$ | Seq ID No. 9 |
| | $V_L$ | Seq ID No. 10 |
| MAb C | $V_H$ | Seq ID No. 5 |
| | $V_L$ | Seq ID No. 6 |
| MAb D | $V_H$ | Seq ID No. 7 |
| | $V_L$ | Seq ID No. 8 | g) Quantification of Recombinant Antibodies in Cell Culture Supernatants

ELISA

Antibodies in cell culture supernatants were quantified using an Enzyme-Linked ImmunoSorbent Assay (ELISA) capturing with an anti-human Fc antibody (Stratech Scientific, Suffolk, UK catalogue number 109-005-098) at a dilution of 1:400 in 2% Marvel in PBS. After washing 3 times in phosphate-buffered saline with Tween (PBST), bound antibody was detected with a peroxidase-coupled anti-human light chain antibody (The Binding Site Ltd, Birmingham, UK catalogue number AP015 (kappa) or AP017 (lambda)) at a dilution of 1:2500 in 2% M-PBS. After washing three times in PBST, 3,3',5,5'-Tetramethylbenzidine (TMB) (Sigma-Aldrich, Dorset, UK) colorimetric substrate was added, the colorimetric reaction was allowed to develop for 6 minutes before stopping with 2M sulphuric acid (VWR (BDH), Leicestershire, UK). Absorbance at 450 nm was measured and antibody concentrations were deduced by comparison with a calibration curve.

Protein A-HPLC

Antibodies in cell culture supernatants were also quantified using protein A-high performance liquid chromatography (PA-HPLC) on an Agilent HP1100 or HP1200 (Agilent Technologies, Santa Clara, Calif., USA) by comparing peak size from each sample with a calibration curve.

Octet

Alternatively antibodies in cell cultures supernatants were quantified using the OctetQ system (Forté Bio, Menlo Park, Calif., USA) with the Protein A quantitation biosensors, according to the manufacturer's instructions.

h) Western Blot Analysis of EBNA-1 Expression

Cells were harvested by centrifugation (800 rpm, 5 minutes, Hereaus Megafuge 1.0) and incubated in lysis buffer [10 mL CytoBuster (Merck, Darmstadt, Germany) plus one Complete Mini Protease Inhibitor tablet (Roche Diagnostics Ltd, Burgess Hill, UK) and 2 µl Benzonase (Roche Diagnostics Ltd, Burgess Hill, UK)] for 10 minutes on ice. After centrifugation at 16,000×g the soluble supernatant was transferred to a fresh tube and stored at −70° C. until needed. Before use, the supernatant (cell extract) was thawed on ice.

SDS-PAGE was performed using the NuPAGE gel system (Invitrogen, Paisley, UK) according to the manufacturer's protocol. Briefly, cell extracts were combined with 5× loading buffer and 2-mercaptoethanol as a reducing agent, incubated at 95° C. for 1 minute and loaded onto 4-12% NuPAGE Novex Bis/Tris gels. Separation of proteins took place in NuPAGE MES SDS running buffer. For electro-transfer of proteins, the iBlot Dry-Blotting system from Invitrogen was used according to the manufacturer's protocol (preset program 2, 6 minute transfer).

After electro-transfer, membranes were blocked in 5% powdered skimmed milk-PBS-Tween (M-PBST) for 1 hour. Mouse monoclonal antibody against EBNA-1 (Calbiochem catalogue number DP15L) was used as the primary antibody at a dilution of 1:1000 in 2.5% M-PBST. After washing for 30 minutes in PBST (at least 2 changes of wash), a peroxidase coupled goat anti-mouse IgG Fc antibody (Alpha Diagnostics catalogue number 40126) was used as a secondary antibody at a dilution of 1:3000 in 2.5% M-PBST.

After washing for 1 hour in PBST (at least 4 changes of wash), bound peroxidase conjugates were detected by chemiluminescence using Amersham ECL Plus Western Blotting Detection reagents and Amersham Hyperfilm ECL (GE Healthcare, Buckinghamshire, UK) and manually developing the film using Kodak developing and fixing reagents.

Quantification of Intracellular Antibody Using Flow Cytometry.

Cells were fixed in mid-log growth phase, typically on three of four days after the previous sub-culture. $1 \times 10^7$ cells at >90% viability were pelleted by centrifugation at 120 g for 5 minutes. Spent cell culture medium was removed by aspiration, and cells washed twice with 5 ml room temperature Dulbecco's PBS (Invitrogen 14190). Cells were resuspended in 5 ml pre-chilled (−20° C.) 70% methanol in PBS. Samples were capped tightly to prevent evaporation and stored at −20° C. Samples were used within 2 months to ensure there was no degradation.

For the detection of GS, fixed cells were probed with a primary antibody against GS (rabbit-anti-GS, ab49873-00, Abcam, Cambridge, UK used at 5 ug/ml) and then a secondary, labelled, antibody against the primary was used as the detection antibody (anti-Rabbit-APC, 111-136-144, Jackson ImmunoResearch Laboratories, PA, USA, used at 2.5 ug/ml).

To stain the cells, $2 \times 10^6$ cells in 70% methanol/PBS (i.e. 1 ml of the sample above) was washed twice with dPBS and then cells resuspended in the diluted primary conjugate. Cells were incubated on ice for 30 minutes and then washed twice with dPBS. The cells were then resuspended in the diluted fluorescently labelled conjugate and incubated in the dark on ice for 30 minutes.

For unstained controls, cells underwent the same process but PBS was used in place of the two antibodies. For secondary-only controls, the primary antibody was substituted with PBS, but the cells were stained with the secondary antibody as described.

Flow cytometry was performed on the FACSCalibur (Becton Dickinson) using standard methods.

EXAMPLE 2

Construction of CHO Cell Lines Expressing EBNA-1 or EBNA-1/GS

It is known that in HEK-293-EBNA cells, the interaction of EBNA-1 and oriP leads to increased product titres. To investigate whether the same effect was seen in CHO cells, a CHO cell line, which constitutively expressed EBNA-1, was created.

To investigate whether there was a metabolic advantage seen in transient transfection using a host cell, which expresses GS, a CHO line which expressed GS as well as EBNA-1 was created.

a) Transfection of CHO Cells with pmCEP4 to Introduce the EBNA-1 Gene or Co-Transfection to Introduce EBNA-1 and GS Genes.

To produce a CHO cell line stably expressing EBNA-1 only, CHO cells were transfected with the pmCEP4 plasmid. After allowing cells to recover overnight, Hygromycin selection to 400 µg/mL was added.

To produce a CHO cell line, which stably expressed both EBNA-1 and GS, CHO cells were co-transfected with pmCEP4 and pSI-GS at a ratio of 3:1. After allowing cells to recover overnight, MSX selection to 50 µM was added. To investigate the role of selection, cells were either selected with 50 µM MSX only or with 50 µM MSX and 200 µg/ml Hygromycin in combination. For double-selected cell lines Hygromycin selection was added after 2 weeks under MSX selection.

After 3-4 weeks, single colonies were identified.

Twenty single colonies for the CHO-EBNA-1 transfection, 20 single colonies for the CHO-EBNA-1/GS MSX-selected transfection and 10 single colonies for the CHO-EBNA-1/GS double-selected transfection were expanded to 24-well plates. After one passage, cells were transferred to T25 cell culture flasks (WorldWide Medical Products, Inc., Hamilton, N.J., USA) and after one further passage expanded to shaking cultures. Cells were then routinely maintained in shaking cultures.

b) Screening of Transfections for a Suitable Host for Transient Protein Production After four to five subcultures in Erlenmeyer flasks, cells from the continuous subculture were transiently transfected as described in materials and methods section. Overgrow supernatants were analysed for expression of the transiently expressed antibody by ELISA as described.

The cell lines with the highest productivity by transient transfection were identified for each transfection and selection method.

The best single transfectant was G22, from the CHO-EBNA-1/GS transfection, selected with MSX only, with a titre of 47 mg/l. From the equivalent transfection which was selected with MSX and Hygromycin, the highest producer was GH5, at around 41 mg/L.

The best transfectant from the CHO-EBNA-1 transfection was C1, with a titre of 28 mg/L, with a number of the transfectants reaching similar titres. FIG. 7 shows the distribution of transfectants from the transfection of CHO cells with EBNA-1, selected with Hygromycin. The highest expressing cell line was C1, with a titre of 28 mg/L.

From this data, the highest expressing cell lines were isolated from transfectants expressing GS and EBNA-1.

d) Western Blot Analysis of Cell Lines with High Transient Expression Efficiency to Confirm Presence of EBNA-1.

In order to confirm that the high expressing cell lines are stably expressing the EBNA-1 protein, cell extracts were probed by Western Blotting using anti-EBNA-1 antibody as described in Example 1. Cell extracts from CHO-EBNA-1 and CHO-EBNA-1/GS cell lines showed a positive band which co-migrates with EBNA-1 protein (Autogen Bioclear UK Ltd, Calne, Wiltshire, UK. Catalogue No: 10-523-001). In contrast the wild type CHO host cell line did not show a detectable band. This is shown in FIG. 6.

EXAMPLE 3

Effect of Transfecting GS into CHO-EBNA-1 Cell Line (C1)

In order to confirm the possible metabolic advantage of over-expressing GS in a CHO-EBNA stable cell line, a CHO cell line stably transfected with EBNA-1 only was transfected with the GS gene.

To eliminate the possibility that an improvement in expression may be attributed to isolation of a high expressing clone from the C1 heterogeneous population, limited dilution cloning of the C1 parental cell line was also carried out.

The CHO-EBNA cell line C1 was transfected by electroporation with the GS gene carried on plasmid pSI-GS. Cells were plated out in 96-well plates with MSX and Hygromycin selection. For limiting dilution cloning of the CHO-EBNA C1 cell line, cells were plated out in 96-well plates at low cell concentrations to ensure a high probability of deriving monoclonal cell lines. After three weeks, 100 colonies from both the transfections and dilution cloning were identified for further analysis. Cells were bulked up to T-flasks, where the productivity of all 200 cell lines was assessed in transient transfection of antibody constructs.

Analysis of the concentration of IgG in the culture supernatants was performed using the Octet system. Cell lines and dilution clones were ranked for productivity and the leading cells from each were bulked up to shake flask cultures. The productivity of these cell lines was again assessed in transient transfection of antibody expression constructs. Data for this set of transfections are shown in FIG. 8. Transfection of the GS gene into the CHO-EBNA backgrounds confers higher antibody expression levels in transient transfection when compared to CHO-EBNA-1 alone. On average, an approximately 2.2-fold increase in productivity is seen. Cloning out of the CHO-EBNA cell line showed little improvement in productivity over the original parental cell line.

FIG. 7 shows the distribution of harvest titres from the 15 clones from the limiting dilution cloning of C1 and the 20 transfectants from the transfection of C1 with the GS gene. For comparison the productivity of the C1 parent (heterogeneous population) is shown. The bar shows the mean titre of the population while the dots show the distribution of titres within the population. For the C1 transfected with GS, the mean is significantly higher than the C1 parent or the C1 dilution clones and the distribution of the transfectants shows a shift in the population towards higher expression levels. Since the only difference between the populations is that the transfectants contain and are selected for the GS gene, the marked improvement in titre can be attributed to the stable co-expression of GS in the EBNA-1 expressing cell lines.

EXAMPLE 4

Evaluation of Antibody Expression in CHO-EBNA/GS and CHO-EBNA Cell Lines

Different stable CHO cell lines were created as host cell lines for transient expression of recombinant protein. They are as follows:
  Cell line C1: transfection of EBNA-1 only, hygromycin selection
  Cell line G22: co-transfection of EBNA-1 and GS constructs, MSX selection only
  Cell line GH5: co-transfection of EBNA-1 and GS constructs, MSX and hygromycin selection
  Cell line C1-GS: sequential transfection of EBNA-1 and GS constructs, MSX and hygromycin selection To confirm the beneficial effect of stable co-expression of GS with EBNA-1 for transient antibody expression in CHO cells lines relative to control CHO (no EBNA-1 or GS) and CHO EBNA-1 cell lines, transient transfections with a panel of antibodies was performed. Three different antibodies MAb-A (IgG γ1,λ) MAb-B (IgG γ2, λ) and MAb-C (IgG γ1, λ) constructs were transiently transfected into these cell lines.

Clarified cultured supernatants from transfections were analysed for expressed antibody by Protein A HPLC.

For all three antibody molecules the stable co-expression of GS with EBNA-1 in the host cell line (G22, GH5 or C1-GS), resulted in increased antibody production levels relative to expression in the host cell line (CHO wild type) or host cell line expressing EBNA-1 alone (C1).

Between the different expressed antibodies there are as expected differing maximum levels of antibody expressed, but in all examples stable co-expression of GS and EBNA-1 leads to elevated expressed antibody.

FIG. 8 shows the expression of three different antibodies (MAb-A, B and C) from different CHO host cell lines. These cell lines include stable CHO cell lines expressing EBNA-1 only or EBNA-1 and GS (C1, G22, GH5 and C1-GS). CHO wild type (without EBNA-1 or GS) was included as control. The cell lines were transiently co-transfected with light chain and heavy chain expression constructs for the appropriate antibodies. Cultures were allowed to over-grow and then clarified culture supernatants were analysed by Protein A HPLC to determine the concentration of antibody produced. Consistently for all three antibodies expressed, stable co-expression of both EBNA-1 and GS led to higher transient expression of antibody in these cell lines relative to host cells stably expressing just EBNA-1 or either EBNA-1 or GS.

EXAMPLE 5

Characterisation of EBNA-1 and EBNA-1/GS Transfected CHO Cells

In order to confirm that the transfected EBNA-1 and GS genes were being expressed and the expression of these genes correlated to the enhanced transient expression, the stably transfected host cell lines, C1, G22 and C1-GS (and control CHO WT cells) were characterised by Quantitative-Reverse Transcriptase-PCR (Q-RT-PCR) to analyse RNA expression of these genes.

Firstly, RNA free of contaminating genomic DNA was prepared from aliquots of $3 \times 10^6$ cells using a Qiagen RNeasy extraction kit (Qiagen, Hilden, Germany) as per kit instructions.

Briefly cells are lysed in a guanidine-thiocyanate-containing buffer, ethanol is added and the sample added to a silica-based membrane column where the RNA binds to the membrane, contaminants are washed away and the purified RNA eluted with water.

Secondly, cDNA was produced by taking 500 ng of RNA and performing Reverse Transcription (RT). The RNA samples in a 50 µl reaction volume with both oligo d(T) and random hexamer primers underwent reverse transcription using Superscript II reverse transcriptase (Invitrogen Life Technologies, Rockville, Md.) as per kit instructions.

For Q-RT-PCR primer sets (forward, reverse and probe) specific for the EBNA-1 and GS genes were designed for a Q-RT-PCR analysis using an ABI Prism 7900HT™ Fast Real-Time PCR system (Applied Biosystems (Life Technologies), Carlsbad, Calif., USA).

| Primer/Probe: | Sequence (5' to 3'): |
|---|---|
| Forward GS PCR primer | AGCCTATGGCAGGGATATCGT (SEQ ID NO: 11) |
| Reverse GS PCR primer | CCTGTAATCTTGACCCCAGC (SEQ ID NO: 12) |
| GS assay probe | AGGCTCACTACCGCGCCTGCTTG (SEQ ID NO: 13) |
| Forward EBNA-1 PCR primer | GGATGCGATTAAGGACCTTGTT (SEQ ID NO: 14) |
| Reverse EBNA-1 PCR primer | CGTCAAAGCTGCACACAGTCA (SEQ ID NO: 15) |

-continued

| Primer/Probe: | Sequence (5' to 3'): |
|---|---|
| EBNA-1 assay probe | TGACAAAGCCCGCTCCTACCTGCA (SEQ ID NO: 16) |

NB.

A CHO specific GAPDH (glyceraldehyde 3-phosphate dehydrogenase) assay was performed to allow normalisation of the data.

Sets of cDNA (RT reactions from the RNA samples) along with no RT controls (to control for carry through of any genomic DNA), were tested with EBNA-1, GS and CHO GAPDH assays. Approximately 25 ng of each RT reaction were tested per Q-PCR well, with each sample tested in duplicate. Reactions were set up based on the TaqMan™ Universal PCR master Mix protocol (Applied Biosystems). All reactions were thermal cycled as follow: 50° C. for 2 minutes, 95° C. for 10 minutes, followed by 40 cycles of 95° C. for 15 seconds, 60° C. for 1 minute. Data was collected and analysed by the ABI Prism 7900™ Sequence Detection system (Applied Biosystems). Relative mRNA levels were determined against a standard curve created from a serial dilution of the target sequence on a plasmid DNA, and expressed as the number of copies of the expressed target gene per nanogram of RNA (normalised against CHO-GAPDH).

Table 1 shows the relative mRNA levels for EBNA-1 and GS in the CHO WT, C1, G22 and C1-GS cell lines.

|  | EBNA-1 mRNA | GS mRNA |
|---|---|---|
| CHO-WT | 0.0 | 0.0 |
| C1 | 7.5 | 7.5 |
| G22 | 33.1 | 1022.9 |
| C1-GS | 7.7 | 1687.5 |

Expression levels for the EBNA-1 and GS genes, were calculated as the number of copies of the expressed target gene per picogram of cDNA detected by the CHO GAPDH normalising assay.

The analysis confirms that there is no detectable level of EBNA expression in the host cells, but the EBNA-1 gene is expressed in the cell lines into which it was transfected. Expression of GS within the host cells is not detected, and within the C1 cells at a very low level. Where GS is transfected into cell lines (G22 and C1-GS) the mRNA levels are 100-200 fold greater than in the C1 cell line.

EXAMPLE 6

Construction of Further CHO Cell Lines Expressing EBNA-1 or EBNA-1/GS

A second round of transfections was performed in order to confirm the incidence of high producers from the EBNA/GS co-transfection.

a) Transfection of CHO Cells with pmCEP4 to Introduce the EBNA-1 Gene or Co-Transfection to Introduce EBNA-1 and GS Genes.

To produce a CHO cell line stably expressing EBNA-1 only, CHO cells were transfected with the pmCEP4 plasmid. After allowing cells to recover overnight, hygromycin selection to 400 µg/mL was added.

To produce a CHO cell line which stably expressed both EBNA-1 and GS, CHO cells were co-transfected with pmCEP4 and pSI-GS at a ratio of 3:1. After allowing cells to recover overnight, selection was added. Cells were selected with 50 µM MSX and then after two weeks under MSX selection, hygromycin selection to 200 µg/mL was added.

After 3-4 weeks, single colonies were identified.

Forty-eight single colonies for the CHO-EBNA-1 transfection, and 48 single colonies for the CHO-EBNA-1/GS double-selected transfection were expanded and continuously subcultured until they were being routinely maintained in shaking cultures.

b) Screening of Transfections for a Suitable Host for Transient Protein Production After two to three subcultures in Erlenmeyer flasks, cells from the continuous subculture were transferred to Cultiflasks (spin-tubes) and transiently transfected as described in materials and methods section. Overgrow supernatants were analysed for expression of the transiently expressed antibody by ELISA as described.

The cell lines with the highest productivity by transient transfection were identified for each transfection and selection method.

FIG. 9 shows the distribution of transfectants from the transfection of CHO cells with EBNA-1, selected with hygromycin. The highest expressing cell line was CEP27, with a titre of 83 mg/L of MAb A.

FIG. 10 shows the distribution of transfectants from the transfection of CHO cells with EBNA-1 and GS, selected with MSX and Hygromycin. The highest expressing cell line was CO16, with a titre of 113 mg/L of MAb A.

FIG. 11 shows a comparison of the spread of titres from each population of transfectants. From this data, the highest expressing cell lines were isolated from transfectants expressing GS and EBNA-1. There is some overlap between the low expressors from the co-transfected population with the high producers from the EBNA-1 only transfection. To determine significance of the differences between the populations, two analyses were carried out. Analytical comparison of the two populations using a two-tailed t-test shows that the difference between the populations is highly significant (P<0.0001). Two-way ANOVA shows significance in the difference between populations (P=0.0066) but not within populations (P=0.6719) (Analysis performed using GraphPad Prism v5.01 for Windows, GraphPad Software Inc, La Jolla, Calif., USA).

d) Comparison of High, Medium and Low Producers from the EBNA-1 Only Transfections and the EBNA-1/GS Transfections.

To allow further, more detailed, comparison of the differences in expression level within and between populations, a few transfectants were selected across the titre range.

For EBNA-1 only transfection, the transfectants selected were:

| Transfectant | Titre in initial screen (mg/L) |
|---|---|
| CEP27 | 83 |
| CEP47 | 60 |
| CEP12 | 24 |
| CEP2 | 12 |
| CEP9 | 12 |
| CEP54 | 12 |
| CEP35 | 8 |
| CEP39 | 8 |
| CEP40 | 8 |

For EBNA-1/GS transfection, the transfectants selected were:

| Transfectant | Titre in initial screen (mg/L) |
|---|---|
| CO16 | 113 |
| CO32 | 110 |
| CO8 | 66 |
| CO27 | 63 |
| CO34 | 58 |
| CO12 | 31 |
| CO23 | 30 |
| CO31 | 29 |
| CO15 | 6 |
| CO18 | 6 |
| CO35 | 6 |

The transfectants in the above tables were revived from liquid nitrogen and continuously subcultured in shaking cultures as described in Example 1. After six subcultures, cell pellets were frozen down for Western Blotting and for QPCR, and cells were passaged for one further subculture without hygromycin before transiently transfecting with MAb A as described in Example 1. Transfected cells were allowed to overgrow for 14 days before taking samples for quantification. Secreted antibody was quantified using Protein A-HPLC as described in Example 1. FIGS. 12 and 13 show the titres from these transient transfections. G22 was included as a positive transfection control and to allow comparison between the transfectants selected in each round c) Western Blot Analysis of Cell Lines with High Transient Expression Efficiency to Confirm Presence of EBNA-1.

In order to determine that expression of the EBNA-1 protein in high, medium and low expressing cells, cell extracts were probed by Western Blotting using anti-EBNA-1 antibody according to the method as described in Example 1. However, in this instance the primary antibody used was mouse IgG1 anti-EBNA Clone M5042521, Stratech Scientific Ltd, Suffolk, UK, catalogue number 10-E40H, diluted to 6 ug/mL in M-PBST). Cell extracts from high expressing CHO-EBNA-1 transfectants showed a positive band which co-migrates with EBNA-1 protein. In contrast the low expressing transfectants and wild type CHO host cell line did not show a detectable band. (FIGS. 14 to 17). These results show that only the cells which express EBNA-1 are capable of high transient antibody expression.

Confirmation of Presence of GS by Flow Cytometry.

The five highest expressing cell lines from the panel of stably co-transfected cells (CO8, CO16, CO23, CO27 and CO32) were analysed by flow cytometry for expression of GS.

Controls were a GS knockout derivative of the CATS cell line (GSKO), the CATS wildtype host (CATS, to determine endogenous GS levels). A null baseline was determined using the CATS host with the secondary antibody only (CATS-control). This gave the level of signal which was due to background only. Each transfectant was compared in turn with the three controls. Cell lines C1 and G22 from the previous round of selections were included; it is known that C1 is negative for endogenous GS and G22 is positive, which allowed comparison of the new cell lines with these known samples.

For all the CO cell lines, the flow results qualitatively indicate that there is expression of transfected GS (FIG. 18). Quantitative RT-PCR Characterisation of EBNA-1 and EBNA-1/GS Transfected CHO Cells In order to confirm that the transfected EBNA-1 and GS genes were being expressed and the expression of these genes correlated to the enhanced transient expression, the stably transfected host cell lines, both CEP only and CEP/GS co-transfected cell lines (and control CAT-S CHO WT cells) were characterised by qRT-PCR to analyse the RNA expression of these genes. The results are shown in FIG. 19.

Isolation of total RNA and cDNA synthesis from 9* CEP only, 12* CEP/GS (includes G22) co-transfection, C1-CEP only cells (internal reference comparator) and CAT-S WT control cells was performed using the TaqMan® Cells-to-CT™ kit from ABI (Applied Biosystems (Life Technologies), Carlsbad, Calif., USA) (performed by Invitrogen as a custom service).

TaqMan Cells-to-CT kit details: This kit enables researchers to easily perform expression analysis using cultured cells without purification of RNA. The kit includes reagents for cell lysis and RNA preservation, genomic DNA removal, and reverse transcription (RT). The kit also includes TaqMan® Gene Expression Master Mix for use in subsequent real-time PCR analysis. Supplied by ABI (Applied Biosystems (Life Technologies), Carlsbad, Calif., USA).

Custom Q-RT-PCR primers and probes specific for the EBNA-1, and GS transcripts were designed using Primer Express v3.0 software (ABI), and the ordered from ABI (Applied Biosystems (Life Technologies), Carlsbad, Calif., USA).

The samples were screened in triplicate wells using the EBNA-1 and GS specific primers/probe sets. The cDNA samples were also screened by qRT-PCR analysis with a control housekeeping gene GAPDH to allow normalisation of the data. Data was collected and analysed by the ABI Prism 7900 Sequence Detection system (Applied Biosystems).

Ct data for both housekeeping and EBNA-1 and GS mRNA were analysed using a $\Delta\Delta Ct$ method normalising data firstly against the housekeeping gene and performing comparative analysis relative to the C1 CEP only cell line (i.e. this cell is set arbitrarily as the baseline for both GS and EBNA-1 expression so its $\Delta\Delta Ct$ value is 1.000 for both GS and EBNA-1 RNA).

REFERENCES

All references cited anywhere in this specification, including those cited anywhere above, are incorporated herein by reference in their entirety and for all purposes.

1 Yates, J. L., Warren, N., Reisman, D. and Sugden, B, *A cis-acting element from the Epstein-Barr viral genome that permits stable replication of recombinant plasmids in latently infected cells*. Proc. Natl. Acad. Sci. USA, 1984. 81: p. 3806-3810

2 Yates, J. L., Warren, N. and Sugden, B., *Plasmids derived from Epstein-Barr virus replicate stably in a variety of mammalian cells*. Nature (London), 1985. 313: p. 812-815

3 Chittenden, T., Lupton, S, and Levine, A., J., *Functional limits of OriP, the Epstein-Barr virus plasmid origin of replication*. Journal of Virology, 1989. 63: p. 3016-3025.

4 Kirchmaier, A. L., and Sugden, B., *Plasmid maintenance of derivatives of OriP of Epstein-Barr virus*. Journal of Virology, 1995. 69(2): p. 1280-1283.

5 Saeki, Y., Wataya-Kaneda, M., Tanaka, K. and Kaneda, Y., *Sustained transgene expression in vitro and in vivo using an Epstein-Barr virus replicon vector system combined with HVJ liposomes*. Gene Therapy, 1998. 5: p. 1031-1037.

6 Cachianes, G., Ho, C., Weber, R. F., Williams, S. R., Goeddel, D. V. and Leung, D. W., *Epstein-Barr virus-derived*

*vectors for transient and stable expression of recombinant proteins.* Biotechniques, 1993. 15(2): p. 255-259.

7 Längle-Rouault, F., Patzel, V., Benavente, A., Taillez, M., Silvestre, N., Bompard, A., Sczakiel, G., Jacobs, E. and Rittner, K., *Up to 100-fold increase of apparent gene expression in the presence of Epstein-Barr virus OriP sequences and EBNA-1: implications of the nuclear import of plasmids.* Journal of Virology, 1998. 72(7): p. 6181-6185.

8 Tomiyasu, K., Satoh, E., Oda, Y., Nishizaki, K., Kondo, M., Imanishi, J. and Mazda, O., *Gene transfer in vitro and in vivo with Epstein-Barr virus-based episomal vector results in markedly high transient expression in rodent cells.* Biochemical and Biophysical Research Communications, 1998. 253: p. 733-738

9 Krysan, P. K., and Calos, M. P., *Epstein-Barr virus-based vectors that replicate in rodent cells.* Gene, 1993. 136: p. 137-143

10 Mizuguchi, H., Hosono, H. and Hayakawa, T., *Long-term replication of Epstein-Barr virus-derived episomal vectors in the rodent cells.* FEBS Letters, 2000. 472: p. 173-178

11 Durocher, Y., Perret, S, and Kamen, A., *High-level and high-throughput recombinant protein production by transient transfection of suspension-growing human 293-EBNA1 cells.* Nucleic Acids Research, 2002. 30(2): p. E9

12 Baldi, L., Muller, N., Picasso, S., Jacquet, R., Girard, P., Thanh, H. P., Derow, E. and Wurm, F. M., *Transient gene expression in suspension HEK-293 cells: Application to large-scale protein production.* Biotechnology Progress, 2005. 21: p. 148-153

13 Baldi, L., Hacker, D. L., Adam, M. and Wurm, F. M., *Recombinant protein production by large-scale transient gene expression in mammalian cells: state of the art and future perspectives.* Biotechnology Letters, 2007. 29: p. 677-684

14 Meissner, P., Pick, H., Kulangra, A., Chatellard, P., Freidrich, K. and Wurm, F. M., *Transient gene expression: recombinant protein production with suspension-adapted HEK293-EBNA cells.* Biotechnology and Bioengineering, 2000. 75(2): p. 197-203.

15 Prett, J., Daramola, L., Cohen, M., Davies, S., Field, R. and Hatton, D., *Rapid production of IgG from ScFv (Poster).* Second European BioTechnology Workshop, Switzerland., 2002.

16 Derouazi, M., Girard, P., Van Tilbourgh, F., Iglesias, K., Muller, N., Bertschinger, M. and Wurm, F. M., *Serum-free large-scale transient transfection of CHO cells.* Biotechnology and Bioengineering, 2004. 87(4): p. 537-545.

17 Muller, N., Derouazi. M., Van Tilborgh, F., Wulhfard, S., Hacker, D. L., Jordan, M and Wurm, F. M., *Scalable transient gene expression in Chinese hamster ovary cells in instrumented and non-instrumented cultivation systems.* Biotechnology Letters, 2007. 29: p. 703-711

18 Liu, C., Dalby, B., Chen, W., Kilzer, J. M. and Chiou, H. C., *Transient transfection for high-level recombinant protein production in suspension cultured mammalian cells.* Molecular Biotechnology, 2008. 39: p. 141-153

19 Kunaparaju, R., Liao, M. and Sunstrom, N.-A., *Epi-CHO, an episomal expression system for recombinant protein production in CHO cells.* Biotechnology and Bioengineering, 2005. 91(6): p. 670-677.

20 Birch, J. R., Mainwaring, D. O. and Racher, A. J., *Use of the glutamine synthetase (GS) expression system for the rapid development of highly productive mammalian cell processes.* Modern Biopharmaceuticals (Ed. Knäblein) (c) 2005 Wiley-VCH Verlag GmbH & co. KGaA, Weinheim, 2005.

21 Sambrook and Russell, *Molecular Cloning: a Laboratory Manual:* 3rd edition, 2001, Cold Spring Harbor Laboratory Press 22 Ausubel et al. eds., *Short Protocols in Molecular Biology: A Compendium of Methods from Current Protocols in Molecular Biology*, John Wiley & Sons, 4$^{th}$ edition 1999

23 Pak et al., Cytotechnology 22 (1996) 139-146

24 Harlow and Lane, Antibodies: A Laboratory Manual, Cold Spring Harbor Laboratory, Cold Spring Harbor N.Y., pp. 726, 1988

25 Köhler and Milstein, Nature, 256:495-497, 1975

26 Holliger & Hudson (2005) Nature Biotechnology 23(9): 1126-1136

27 Persic, L., Roberts, A., Wilton, J., Cattaneao, A., Bradbury, A. Hoogenboon, H. R. Gene 187 (1997) 9-18

28 Aiyar, A., Aras, S., Washington, A., Singh, G. and Luftig, R. B. (2009). *Virology Journal.* 6:29.

---

The invention claimed is:

1. An expression-enhanced Chinese Hamster Ovary (CHO) cell line derived from a parent CHO cell line, the expression-enhanced CHO cell line comprising a stably transfected nucleic acid encoding Epstein-Barr Virus Nuclear Antigen 1 (EBNA-1) or a functional truncated variant thereof; and further comprising a stably transfected nucleic acid encoding an exogenous glutamine synthetase.

2. The expression-enhanced CHO cell line of claim 1, wherein the Epstein-Barr Virus (EBV) Nuclear Antigen 1 (EBNA-1) and/or glutamine synthetase (GS) are constitutively expressed in the cell line.

3. The expression-enhanced CHO cell line of claim 1, wherein the cell line further comprises nucleic acid encoding an exogenous polypeptide.

4. The expression-enhanced CHO cell line of claim 3, wherein the nucleic acid encoding the exogenous polypeptide is located trans relative to the nucleic acid encoding EBNA-1 and/or the nucleic acid encoding GS.

5. The expression-enhanced CHO cell line of claim 3, wherein the nucleic acid encoding the exogenous polypeptide further encodes an EBNA-1 binding sequence.

6. The expression-enhanced CHO cell line of claim 3, wherein the exogenous polypeptide is not glutamine synthetase and/or EBNA-1.

7. The expression-enhanced CHO cell line of claim 3, wherein the nucleic acid encoding the exogenous polypeptide is episomal.

8. The expression-enhanced CHO cell line of claim 3, wherein one or more selection markers are provided on the nucleic acid encoding the exogenous polypeptide and optionally wherein the selection markers are not nucleic acid encoding a glutamine synthetase.

9. A kit for exogenous polypeptide expression comprising:
  a) an expression-enhanced CHO cell line according to claim 1; and
  b) an expression vector comprising nucleic acid encoding an EBV origin of replication (oriP) and an exogenous polypeptide relative to the cell line.

10. The expression-enhanced CHO cell line of claim 3, wherein the exogenous polypeptide is an antibody heavy chain and/or an antibody light chain, or an antigen binding fragment thereof.

11. The expression-enhanced CHO cell line of claim 4, wherein the exogenous polypeptide is an antibody heavy chain and/or an antibody light chain, or an antigen binding fragment thereof.

12. The expression-enhanced CHO cell line of claim 5, wherein the exogenous polypeptide is an antibody heavy chain and/or an antibody light chain, or an antigen binding fragment thereof.

13. The expression-enhanced CHO cell line of claim 7, wherein the exogenous polypeptide is an antibody heavy chain and/or an antibody light chain, or an antigen binding fragment thereof.

14. The expression-enhanced CHO cell line of claim 8, wherein the exogenous polypeptide is an antibody heavy chain and/or an antibody light chain, or an antigen binding fragment thereof.

15. The expression-enhanced CHO cell line of claim 3, wherein the exogenous polypeptide is selected from any one of the group comprising prodrug, enzyme, enzyme fragment, enzyme inhibitor, enzyme activator, biologically active polypeptide, hedgehog protein, bone morphogenetic protein, growth factor, erythropoietin, thrombopoietin, G-CSF, interleukin, interferon, immunoglobulin, and immunoglobulin fragment, or combinations thereof.

16. The expression-enhanced CHO cell line of claim 4, wherein the exogenous polypeptide is selected from any one of the group comprising prodrug, enzyme, enzyme fragment, enzyme inhibitor, enzyme activator, biologically active polypeptide, hedgehog protein, bone morphogenetic protein, growth factor, erythropoietin, thrombopoietin, G-CSF, interleukin, interferon, immunoglobulin, and immunoglobulin fragment, or combinations thereof.

17. The expression-enhanced CHO cell line of claim 5, wherein the exogenous polypeptide is selected from any one of the group comprising prodrug, enzyme, enzyme fragment, enzyme inhibitor, enzyme activator, biologically active polypeptide, hedgehog protein, bone morphogenetic protein, growth factor, erythropoietin, thrombopoietin, G-CSF, interleukin, interferon, immunoglobulin, and immunoglobulin fragment, or combinations thereof.

18. The expression-enhanced CHO cell line of claim 7, wherein the exogenous polypeptide is selected from any one of the group comprising prodrug, enzyme, enzyme fragment, enzyme inhibitor, enzyme activator, biologically active polypeptide, hedgehog protein, bone morphogenetic protein, growth factor, erythropoietin, thrombopoietin, G-CSF, interleukin, interferon, immunoglobulin, and immunoglobulin fragment, or combinations thereof.

19. The expression-enhanced CHO cell line of claim 8, wherein the exogenous polypeptide is selected from any one of the group comprising prodrug, enzyme, enzyme fragment, enzyme inhibitor, enzyme activator, biologically active polypeptide, hedgehog protein, bone morphogenetic protein, growth factor, erythropoietin, thrombopoietin, G-CSF, interleukin, interferon, immunoglobulin, and immunoglobulin fragment, or combinations thereof.

* * * * *